(12) United States Patent
Barauskas et al.

(10) Patent No.: US 11,135,264 B2
(45) Date of Patent: *Oct. 5, 2021

(54) FORMULATIONS CONTAINING A SOMATOSTATIN RECEPTOR AGONIST

(71) Applicant: CAMURUS AB, Lund (SE)

(72) Inventors: Justas Barauskas, Lund (SE); Catalin Nistor, Lund (SE); Markus Johnsson, Lund (SE)

(73) Assignee: CAMURUS AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/908,055

(22) Filed: Jun. 22, 2020

(65) Prior Publication Data

US 2021/0008151 A1    Jan. 14, 2021

Related U.S. Application Data

(63) Continuation of application No. 16/361,622, filed on Mar. 22, 2019, now Pat. No. 10,688,148, which is a continuation of application No. PCT/EP2017/074420, filed on Sep. 26, 2017.

(30) Foreign Application Priority Data

Sep. 27, 2016 (EP) ..................... 16190892
Sep. 27, 2016 (GB) ..................... 1616366

(51) Int. Cl.
| | | |
|---|---|---|
| *A61K 38/08* | (2019.01) | |
| *A61K 47/10* | (2017.01) | |
| *A61K 47/14* | (2017.01) | |
| *A61K 47/18* | (2017.01) | |
| *A61K 47/24* | (2006.01) | |
| *A61K 9/00* | (2006.01) | |

(52) U.S. Cl.
CPC ............ *A61K 38/08* (2013.01); *A61K 9/0019* (2013.01); *A61K 47/10* (2013.01); *A61K 47/14* (2013.01); *A61K 47/183* (2013.01); *A61K 47/186* (2013.01); *A61K 47/24* (2013.01)

(58) Field of Classification Search
CPC .... A61K 38/08; A61K 9/0019; A61K 47/186; A61K 47/24; A61K 47/183; A61K 47/14; A61K 47/10
See application file for complete search history.

(56) References Cited

U.S. PATENT DOCUMENTS

| | | | |
|---|---|---|---|
| 5,874,105 A | 2/1999 | Watkins et al. | |
| 8,945,543 B2 | 2/2015 | Igawa et al. | |
| 10,688,148 B2 * | 6/2020 | Barauskas ............ | A61K 38/08 |
| 2007/0185330 A1 | 8/2007 | Walker | |
| 2011/0230569 A1 | 9/2011 | Nistor et al. | |
| 2014/0162944 A1 | 6/2014 | Tiberg et al. | |

FOREIGN PATENT DOCUMENTS

| | | |
|---|---|---|
| JP | 78013357 | 5/1978 |
| JP | 2002356464 A | 12/2002 |
| JP | 2016-504353 A | 2/2016 |
| RU | 2373936 C2 | 11/2009 |
| WO | 97/41834 A1 | 11/1997 |
| WO | 2005/014777 A1 | 2/2005 |
| WO | 2005/117830 A1 | 12/2005 |
| WO | 2006/075123 A1 | 7/2006 |
| WO | 2006/075124 A1 | 7/2006 |
| WO | 2006/075125 A1 | 7/2006 |
| WO | 2006/131730 A1 | 12/2006 |
| WO | 2006/132363 A1 | 12/2006 |
| WO | 2010/020794 A1 | 2/2010 |
| WO | 2010/095964 A1 | 8/2010 |
| WO | 2012/160213 A1 | 11/2012 |
| WO | 2013/083459 A1 | 6/2013 |
| WO | 2013/083460 A1 | 6/2013 |
| WO | 2013/174978 A1 | 11/2013 |
| WO | 2014/016428 A1 | 1/2014 |
| WO | 2014/104791 A1 | 7/2014 |
| WO | 2016/066655 A1 | 5/2016 |
| WO | 2016/102683 A1 | 6/2016 |
| WO | 2018/060212 A1 | 4/2018 |
| WO | 2018/060213 A1 | 4/2018 |

OTHER PUBLICATIONS

International Search Report and Written Opinion in International Application No. PCT/EP2017/074418, dated Dec. 22, 2017.
European Search Report in Application No. 16190892.6, dated Mar. 23, 2017.
Saito et al., "Highly pure aminopolycarboxylic acids of limited metal contents and their salts useful as processing agents for board surface of semiconductors," Database WPI, Section Ch, Week 200314, Thomson Scientific, XP002776439 (2017).
Scott et al., "Demineralization in Organic Solvents by Alkylammonium Salts of Ethylendiaminetetra-acetic Acid," Biochem. J. 169:697-701 (1978).

(Continued)

*Primary Examiner* — Sudhakar Katakam
(74) *Attorney, Agent, or Firm* — J.A. Lindeman & Co., PLLC

(57) ABSTRACT

The present invention relates to pre-formulations comprising:
a) at least one di-acyl lipid;
b) at least one phospholipid;
c) at least one biocompatible, organic solvent;
d) an alkyl ammonium EDTA salt; and
e) at least one somatostatin receptor agonist;

Figure 1:
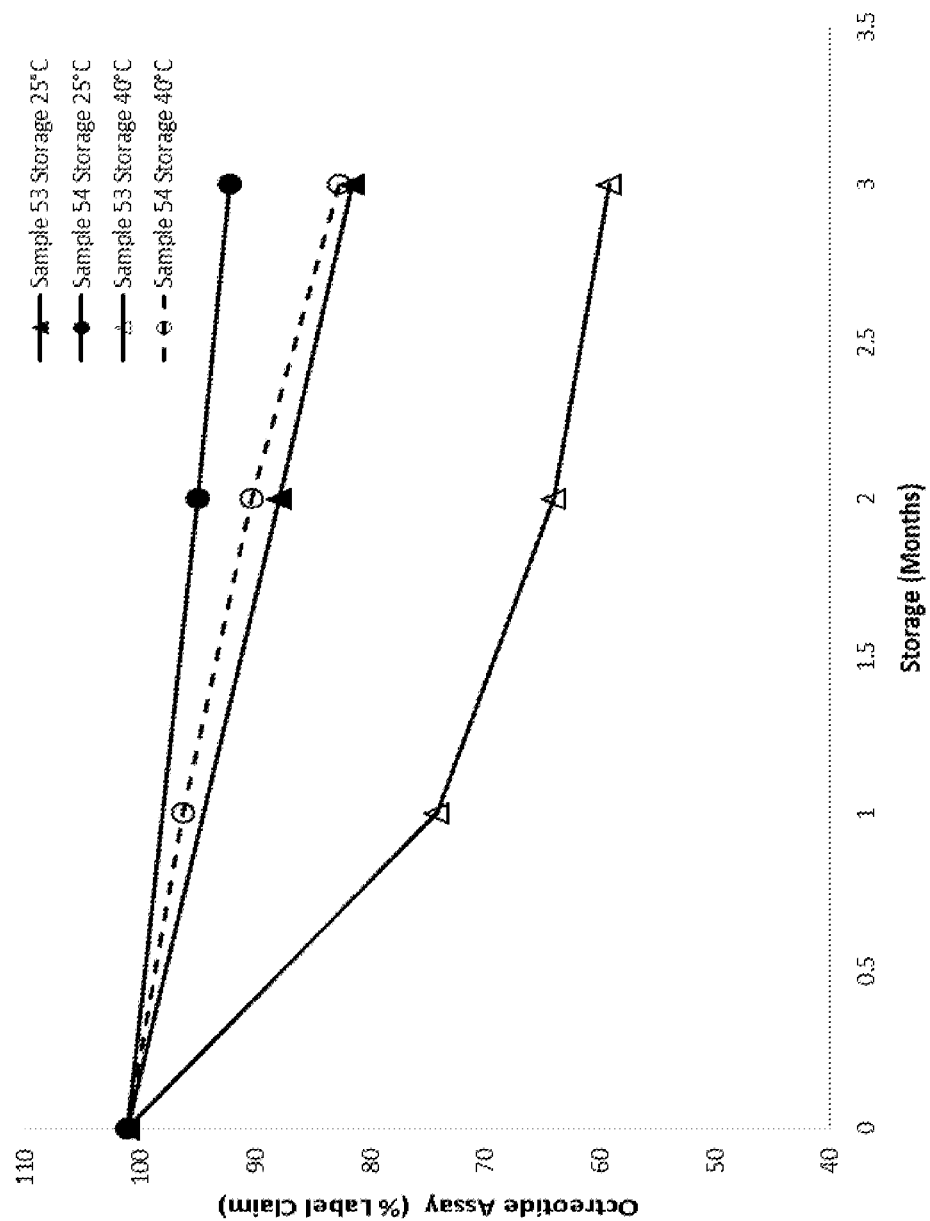

wherein the pre-formulation has a water content in the range of 0 to 1.0 wt %.

The invention further relates to methods of treatment comprising administration of such pre-formulations, to pre-filled administration devices and kits containing the formulations, to the use of an alkylammonium EDTA salt to reduce the decomposition of the lipid components and/or any active agent contained within the pre-formulation.

32 Claims, 11 Drawing Sheets

(56) References Cited

OTHER PUBLICATIONS

International Search Report and Written Opinion of International Application No. PCT/EP2017/074420, dated Dec. 11, 2017.
Shamshina et al., Expert Opinion on Drug Delivery, 2013, 10(10):1367-1381.
Patel et al., Appl Biochem Biotechnol, 2014, 172:3701-3720.
D.A. Harkevich, Pharmacology, Moscow, Medicina, 1987, pp. 47-48, English translation of relevant parts.
Krasniuk I.I., Mikhailova G.V., Chizhova E.T. Pharmaceutical Technology: Technology of Dosage Forms. 2nd edition//Moscow, Academiya, 2006, pp. 297-299, English translation of relevant parts.
Scott and Kyffin, "Demineralization in Organic Solvents by Alkylammonium Salts of Ethylenediaminetetra-acetic Acid", Biochem. J., 1978, vol. 169, pp. 697-701.

* cited by examiner

FORMULATIONS CONTAINING A SOMATOSTATIN RECEPTOR AGONIST

CROSS-REFERENCE TO RELATED APPLICATIONS

This application is a continuation application of U.S. application Ser. No. 16/361,622, filed on Mar. 22, 2019, which is a continuation of International Application No. PCT/EP2017/074420, filed on Sep. 26, 2017, which claims priority to EP. Application No. 16190892.6, filed on Sep. 27, 2016 and GB Application No. 1616366.9, filed on Sep. 27, 2016, each of which is incorporated herein by reference.

FIELD OF THE INVENTION

The present invention relates to formulation precursors (pre-formulations) that upon exposure to water or aqueous media, such as body fluids, spontaneously undergo a phase transition thereby forming a controlled release matrix. In particular, the invention relates to pre-formulations and compositions comprising a somatostatin receptor agonist, said pre-formulations and compositions having an improved resistance to oxidation.

BACKGROUND TO THE INVENTION

Many bioactive agents including pharmaceuticals, nutrients, vitamins and so forth have a "functional window". That is to say that there is a range of concentrations over which these agents can be observed to provide some biological effect. Where the concentration in the appropriate part of the body (e.g. locally or as demonstrated by serum concentration) falls below a certain level, no beneficial effect can be attributed to the agent. Similarly, there is generally an upper concentration level above which no further benefit is derived by increasing the concentration. In some cases increasing the concentration above a particular level results in undesirable or even dangerous effects.

Some bioactive agents have a long biological half-life and/or a wide functional window and thus may be administered occasionally, maintaining a functional biological concentration over a substantial period of time (e.g. 6 hours to several days). In other cases the rate of clearance is high and/or the functional window is narrow and thus to maintain a biological concentration within this window regular (or even continuous) doses of a small amount are required. This can be particularly difficult where non-oral routes of administration (e.g. parenteral administration) are desirable or necessary, since self-administration may be difficult and thus cause inconvenience and/or poor compliance. In such cases it would be advantageous for a single administration to provide active agent at a therapeutic level over the whole period during which activity is needed.

Some patients undergoing treatment will typically require a therapeutic dose to be maintained for a considerable period and/or ongoing treatment for many months or years. Thus a depot system allowing loading and controlled release of a larger dose over a longer period would offer a considerable advantage over conventional delivery systems.

Certain of the formulations of the present invention generate a non-lamellar liquid crystalline phase following administration. The use of non-lamellar phase structures (such as liquid crystalline phases) in the delivery of bioactive agents is now relatively well established. A most effective lipid depot system is described in WO2005/117830, and a highly preferred lipid depot is described in that document. However, there remains scope for achieving depot formulations having improved performance in several respects.

Lipid controlled-release delivery systems have been developed with active agents including GLP-1 (WO2006/131730), somatostatin analogues (WO2006/075124), LHRH analogues (WO2006/075125), as well as non-peptides such as buprenorphine (WO2014/016428). Lipid systems are also of value in treatment in their own right and need not include active agents. For example, the FDA approved oral liquid Episil® alleviates the pain caused by oral mucositis and other inflammatory conditions of the mouth by forming a lipid barrier in the oral cavity, but does not require any active agent.

A particularly versatile combination of lipids is glycerol dioleate (GDO) and phosphatidyl choline (PC). However, sustained released formulations can be produced with a wide variety of other lipid components including tocopherol (WO2006/075123), derivatives of sorbitol (WO2016/102683), triglycerides (WO2016/066655), and a variety of phospholipid components including phosphatidyl ethanolamines (WO2013/083459 and WO2013/083460).

Both the lipid components, particularly unsaturated lipids, and any active agent contained in the pre-formulation or sustained release composition are susceptible to oxidation, either during storage or in vivo. It is desirable to decrease the extent of oxidation since oxidation processes may reduce the content of active agent and/or contribute to the formation of unwanted decomposition products. This in turn reduces the shelf life of a product.

One particular factor contributing to oxidation in lipid compositions is the presence of trace amounts of metal ions, particularly transition metals such as iron (Fe). Even when the lipid components are of high purity grade it is often difficult to entirely remove traces of such ions. It is thought that equipment used for the manufacture of lipid formulations commonly includes stainless steel which can leach small amounts of metal ions (particularly Fe) into the mixture. It is therefore common to include an antioxidant in lipid formulations. These generally function by chelating any metal ions, thereby hindering their participation in oxidation processes.

It is a prerequisite that any antioxidant must be soluble in the lipid pre-formulation. It is described in WO2012/160213 that a carefully controlled amount of water can be included in lipid pre-formulations without causing a phase change into a liquid crystalline phase. In pre-formulations containing an appreciable aqueous content, it may be possible to include an effective amount of a water-soluble antioxidant such as ascorbic acid, inorganic salts of metal chelators, such as ethylenediaminetetraacetic acid (EDTA) (e.g. sodium or calcium salts) and citric acid. However, for certain active agents it may be necessary to avoid prolonged exposure to water during storage (e.g. because the active agent is moisture sensitive), or a more desirable release profile may be obtained without the inclusion of water in the pre-formulation. The present inventors have established that certain somatostatin receptor agonists are less stable in formulations containing water. The avoidance of water may also reduce the amount of trace metals which may be present, since metal ions are generally more soluble in water than in an organic solvent or lipid environment. In lipid formulations having a low water content it is not possible to use conventional water-soluble antioxidants since these may not have the requisite solubility in a substantially water-free lipid environment. It would therefore be advantageous to provide an antioxidant which is soluble in a substantially water-free lipid environment and which limits or prevents the oxidative degradation of the lipid components of the pre-formulation, and any active agent contained within. This is particularly the case for metal chelating agents such as EDTA where the standard inorganic salts (sodium or calcium) are non-soluble or have negligible solubility in non-aqueous environments (e.g. lipid matrices).

WO2010/020794 describes thiolated antioxidants as offering particular advantages in lipid systems and suggests that these are also suitable in non-aqueous lipid systems. However, for certain end uses the presence of a thiolated antioxidant may not be acceptable. This particularly applies, for example, to peptides or proteins having thiolated groups or disulphide bridges. WO2010/020794 also mentions the possibility of including EDTA or the sodium, disodium and calcium disodium salts of EDTA as chelating agent although this is not an option which is exemplified. The present inventors have established that EDTA or the common salts thereof are not soluble to any appreciable extent in the types of lipid formulations described in WO2010/020794, i.e. those based on GDO, SPC and an organic solvent such as ethanol.

It has now surprisingly been established that effective amounts of alkylammonium salts of EDTA can be dissolved in a non-aqueous lipid environment, and that the resulting pre-formulations are highly resistant to oxidative decomposition during storage. Furthermore, although alkylammonium EDTA salts are believed to have an effect on decreasing the decomposition by the expected mechanism of sequestering metal ions, the present invention may in some embodiments improve oxidation resistance above the level that can be accounted for solely by this mechanism.

The inventors have established that the inclusion of alkylammonium EDTA salts can prevent, or substantially decrease the rate of, oxidation of a wide variety of lipid components and/or active agents contained therein. The inventors have found that the inclusion of alkylammonium EDTA can substantially reduce the loss of assay of somatostatin receptor agonists in drug samples tested in stability studies and thus increases shelf-life of the drug product. EDTA salts have the advantage that they are inexpensive, easily produced with a wide variety of counter-cations, and are generally regarded as safe (and are widely used e.g. in pharmaceutical applications).

The stabilizing and shelf-life extending effect of alkylammonium EDTA as found by the inventors may be not only related to the prevention or reduction of oxidation reactions but may be also related to the prevention or reduction of other chemical degradation reactions, e.g. hydrolysis, acylation, deamidation.

SUMMARY OF THE INVENTION

The present invention provides a pharmaceutical formulation comprising an appropriate combination of lipid excipients, organic solvent, alkylammonium EDTA salt and a somatostatin receptor agonist that can be used as a depot-precursor formulation (referred to herein for brevity as a pre-formulation) to address one or more of the needs described above.

In a first aspect, the invention therefore provides a pre-formulation comprising:
  a) at least one di-acyl lipid; b) at least one phospholipid;
  c) at least one biocompatible, organic solvent;
  d) an alkyl ammonium EDTA salt; and
  e) at least one somatostatin receptor agonist;
wherein the pre-formulation has a water content in the range of 0 to 1.0 wt %.

Pre-formulations according to the invention preferably form, or are capable of forming, at least one liquid crystalline phase structure upon contact with excess aqueous fluid.

In a second aspect, the invention provides a pre-formulation comprising: a lipid controlled-release matrix comprising:
  a) at least one of a di-acyl lipid;
  b) at least one phospholipid;
  c) at least one biocompatible, organic solvent;
  d) an alkyl ammonium EDTA salt;
  e) at least one somatostatin receptor agonist;
wherein the pre-formulation has a water content in the range of 0 to 1.0 wt %; wherein the pre-formulation forms, or is capable of forming, at least one liquid crystalline phase structure upon contact with excess aqueous fluid.

A particularly preferred combination of components is glycerol dioleate (GDO), phosphatidyl choline (PC), ethanol, tetrakis(ethanolammonium) EDTA, and octreotide.

The pre-formulations are highly useful for the controlled and sustained release of an active agent, especially those requiring or benefiting from a very flat release profile and/or minimal "burst" upon administration. In a corresponding embodiment, the invention therefore provides for a mixture of:
a lipid controlled-release matrix comprising:
  a) at least one of a di-acyl lipid;
  b) at least one phospholipid;
  c) at least one biocompatible, organic solvent;
  d) an alkyl ammonium EDTA salt; and
  e) at least one somatostatin receptor agonist;
wherein the pre-formulation has a water content in the range of 0 to 1.0 wt %; in the manufacture of a pre-formulation for use in the sustained administration of said active agent. In a preferred embodiment, the pre-formulation forms, or is capable of forming, at least one liquid crystalline phase structure upon contact with excess aqueous fluid.

A "a somatostatin receptor agonist" as referred to herein, may be any compound having agonistic function at one or more somatostatin receptors (SSTRs). There are five known types of SSTRs (SSTR1-SSTR5), showing equally high affinity for SST-14 (see below for description of SST-14). The most investigated somatostatin receptor agonists, including octreotide, show high selectivity for SSTR2 and SSTR5. Thus in one preferred embodiment, somatostatin agonists as indicated herein have an agonistic function at somatostatin receptors including SSTR2 and/or SSTR5.

Preferred somatostatin receptor agonists herein are SST-14, SST-28, octreotide, lanreotide, vapreotide, pasireotide (SOM230) and related peptides. More preferred somatostatin receptor agonists herein are octreotide and pasireotide (SOM230). Most preferred somatostatin receptor agonist herein is octreotide.

Typically the somatostatin receptor agonist will be formulated at a level sufficient to provide an in vivo concentration at a functional level. The somatostatin receptor agonist may be either a natural or synthetic somatostatin receptor agonist which provides a therapeutic, palliative and/or prophylactic effect when administered to a suitable subject (typically being one in need of such an effect).

In a further embodiment, the invention therefore provides a method for the treatment of a human or non-human mammalian subject comprising administering to said subject a pre-formulation as described herein. Such a method may be for the treatment of a human or non-human mammalian subject in need thereof to combat, (e.g. cure, improve, prevent or ameliorate the symptoms of) at least one condition selected from acromegaly, cancers, carcinomas, melanomas, tumours expressing at least one somatostatin receptor, sst(2)-positive tumours, sst(5)-positive tumours, prostate cancers, gastro-entero-pancreatic endocrine tumours, gastro-entero-pancreatic neuroendocrine (GEP NE) tumours (GEP-NET), lung neuroendocrine tumours (lung NET), carcinoid tumours, insulinomas, gastrinomas, vasoactive intestinal peptide (VIP) tumours and glucagonomas, TSH-secreting pituitary adenomas, elevated growth hormone (GH), elevated insulin-like growth factor I (IGF-I), varicial bleeding (especially espohageal), chemotherapy induced gastro intestinal problems (such as diarrhea), lymphorrhea, diabetic retinopathy, thyroid eye disease, obesity, pancreatitis, and related conditions.

The pre-formulations as described herein for use in such methods form a further aspect of the invention.

Correspondingly, in a further aspect, the present invention provides the use of a low viscosity pre-formulation comprising a mixture of:
a) at least one di-acyl lipid;
b) at least one phospholipid;
c) at least one biocompatible, organic solvent;
d) an alkylammonium EDTA salt; and
e) at least one somatostatin receptor agonist;
wherein the pre-formulation has a water content in the range of 0 to 1.0 wt %; in the manufacture of a low viscosity pre-formulation medicament for use in the in vivo formation of a depot for treatment of at least one condition selected from acromegaly, cancers, carcinomas, melanomas, tumours expressing at least one somatostatin receptor, sst(2)-positive tumours, sst(5)-positive tumours, prostate cancers, gastro-entero-pancreatic endocrine tumours, gastro-entero-pancreatic neuroendocrine (GEP NE) tumours, lung NE tumours (lung NET), carcinoid tumours, insulinomas, gastrinomas, vasoactive intestinal peptide (VIP) tumours and glucagonomas, TSH-secreting pituitary adenomas, elevated growth hormone (GH), elevated insulin-like growth factor I (IGF-I), varicial bleeding (especially espohageal), chemotherapy induced gastro intestinal problems (such as diarrhea), lymphorrhea, diabetic retinopathy, thyroid eye disease, obesity, pancreatitis, and related conditions.

One of the advantages of the formulations of the present invention over many other controlled-release compositions is that they are stable to storage in their final form and thus little or no preparation is required at the time of administration. This allows the pre-formulations to be ready-to-administer and also to be supplied in convenient, ready-to-administer form. In a further aspect, the invention therefore provides a pre-filled administration device containing a pre-formulation as described herein. Such a device will generally provide either a single administration or multiple administrations of a composition which will deliver, for example, a dosage of active agent in the range of 1 μg to 15 mg/day, such as 0.1 mg to 15 mg/day or 1 μg to 5 mg/day.

In a further aspect the invention provides a kit comprising said administration device according to the invention.

The kit can optionally contain instructions for subcutaneous or intramuscular administration of said pre-formulation. All pre-formulation described herein are suitable for use in such a kit and may thus be contained therein.

The kits of the invention can optionally include additional administration components such as needles, swabs, and the like and will optionally contain instructions for administration.

BRIEF SUMMARY OF THE ATTACHED FIGURES

FIG. 1. Octreotide assay of Samples 53-54 as a function of time at storage conditions 25° C./60% RH and 40° C./75% RH.

Figure 2:
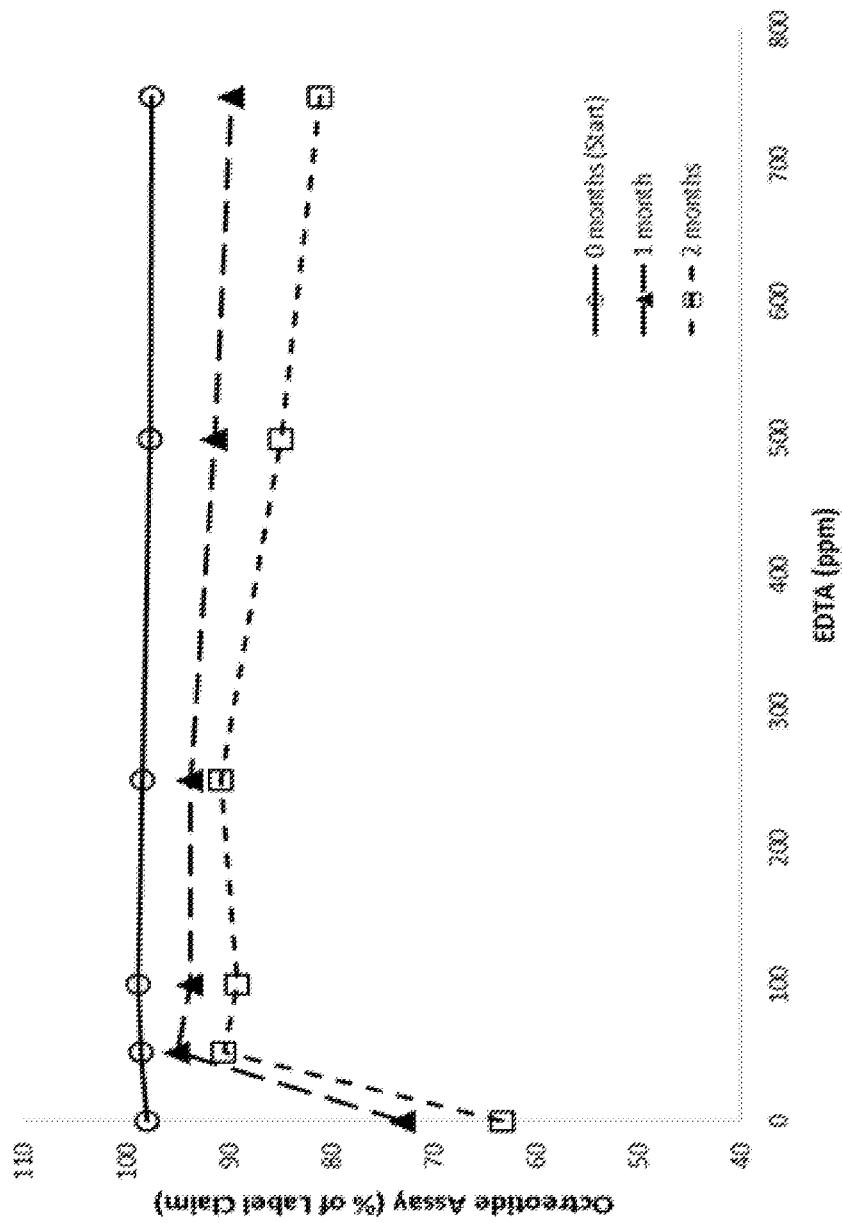

FIG. 2. Octreotide assay of Samples 55-60 as a function of EDTA concentration (0-750 ppm or 0-0.075 wt %) at three time points (0, 1 and 2 months) after storage at 40° C./75% RH.

Figure 3:
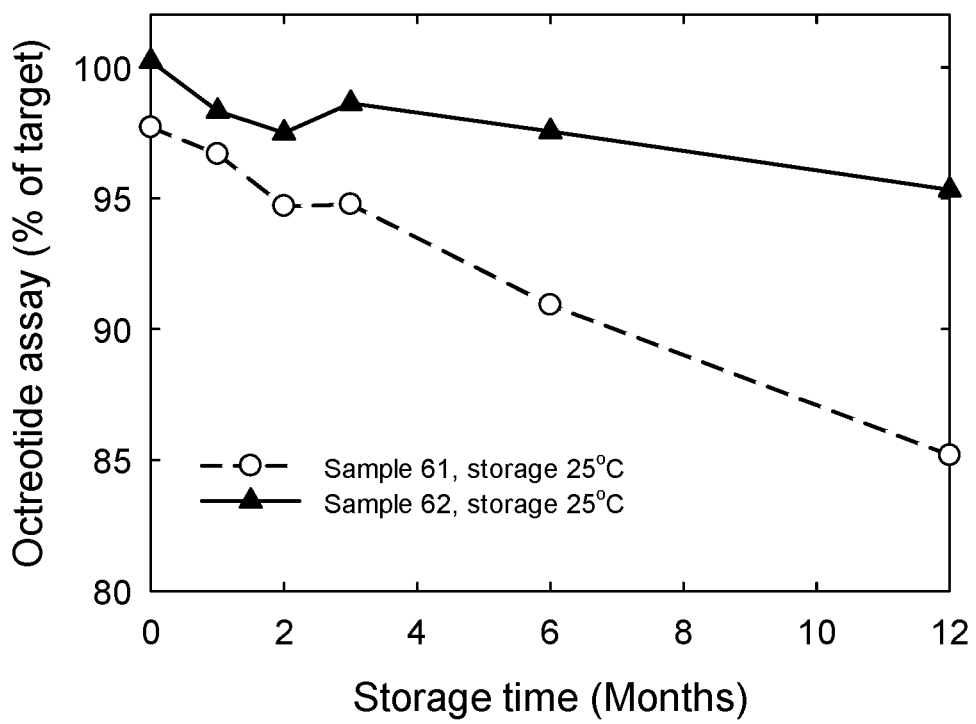

FIG. 3. OCT assay in SPC/GDO/EtOH/PG based formulations in the absence (Sample 61) and presence of 100 ppm EDTA (Sample 62) as a function of time at 25° C./60% RH. Formulations were stored in pre-filled glass syringes.

Figure 4:
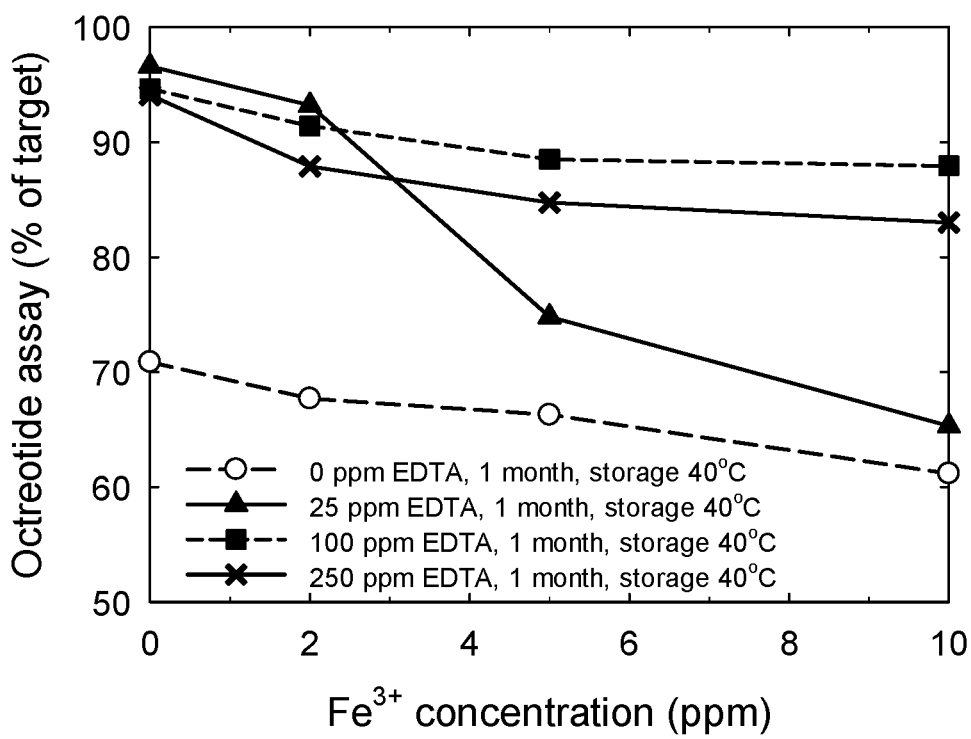

FIG. 4. OCT assay in SPC/GDO/EtOH/PG based formulations as a function of $Fe^{3+}$ concentration in the presence of 0, 25, 100 and 250 ppm EDTA (Samples 63-78) recorded at 1 month of storage at 40° C./75% RH. Formulations were stored in vials with ambient air in the headspace.

Figure 5:
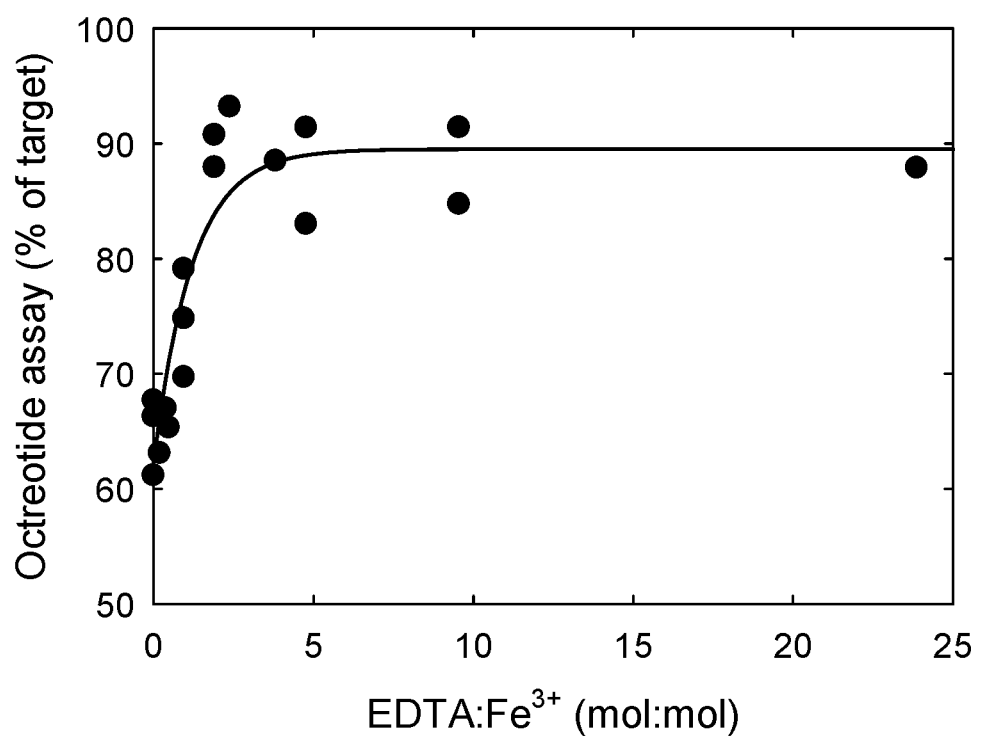

FIG. 5. OCT assay data in SPC/GDO/EtOH/PG formulations as a function EDTA:$Fe^{3+}$ molar ratio after 1 month of storage at 40° C./75% RH. Formulations were stored in vials with ambient air in the headspace.

Figure 6:
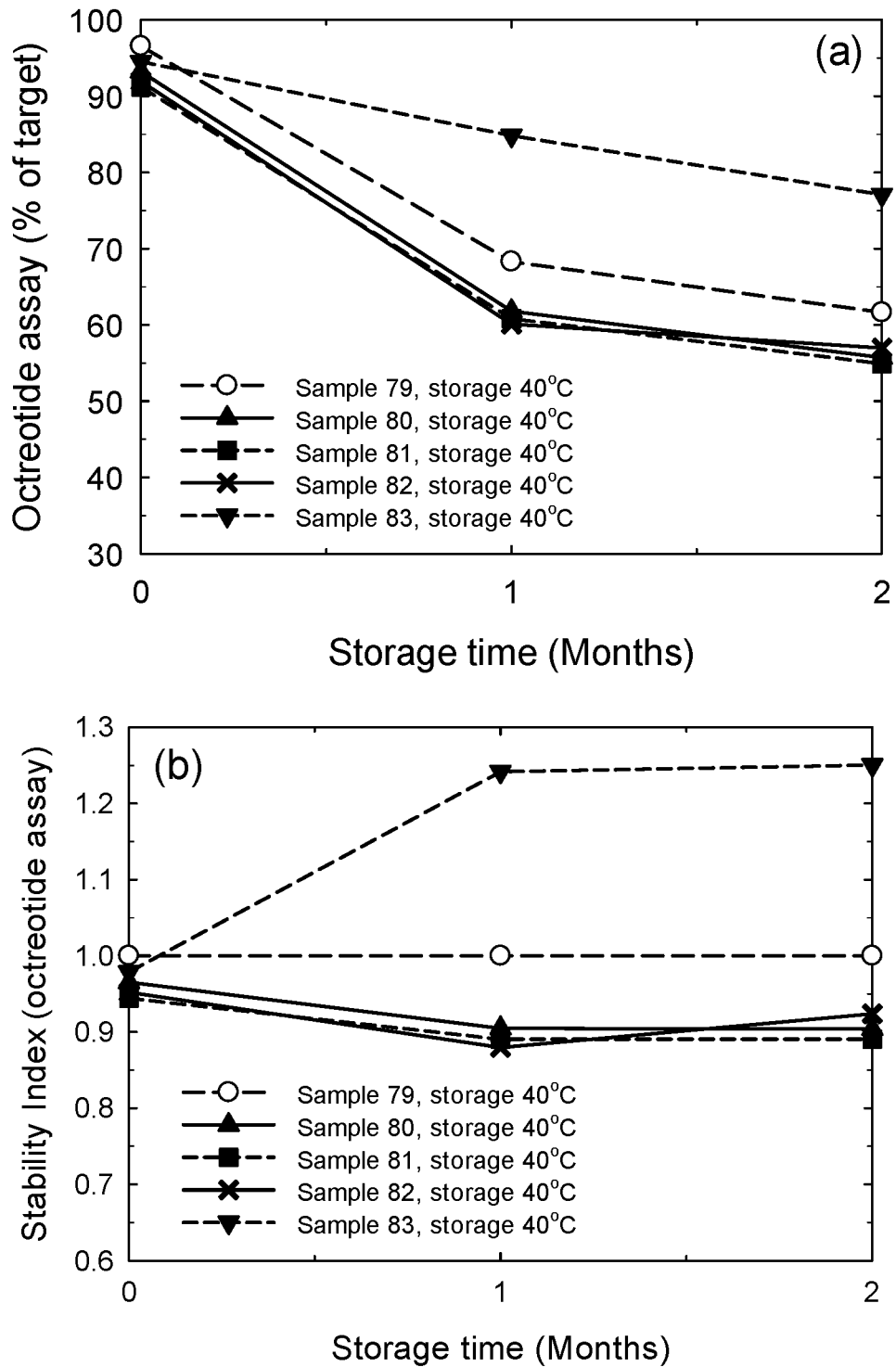

FIG. 6. Assay (a) and Stability Index (b) values of OCT in SPC/GDO/EtOH/PG formulations as a function of time at 40° C./75% RH: without additives (Sample 79, reference), with EDTA (Na) (Sample 80), with EDTA (Na)/ETA (Sample 81), with EDTA (Sample 82), and with EDTA/ETA (Sample 83). Formulations were stored in vials with normal air in the headspace. Except for the reference Sample 79, all formulations also contained 5 ppm $Fe^{3+}$.

Figure 7:
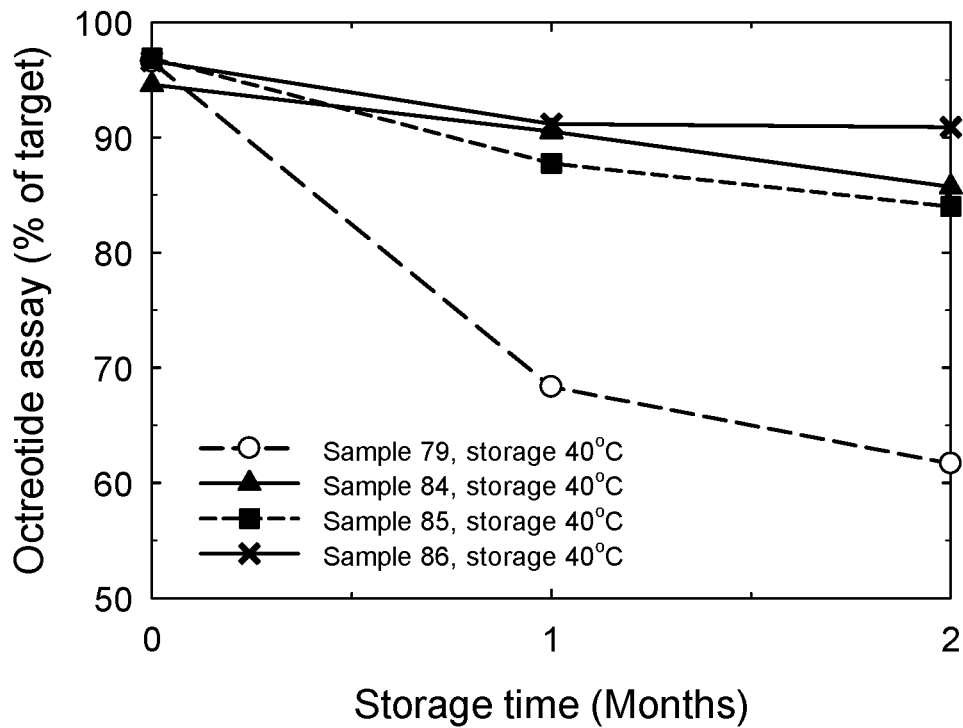

FIG. 7. OCT assay in SPC/GDO/EtOH/PG based formulations in the absence (Sample 79) and presence of 100 ppm EDTA solubilized in the lipid formulation by the use of ETA (Sample 84), DiETA (Sample 85) or ethylenediamine (Sample 86) as a function of time at 40° C./75% RH. Formulations were stored in vials with normal air in the headspace.

Figure 8:
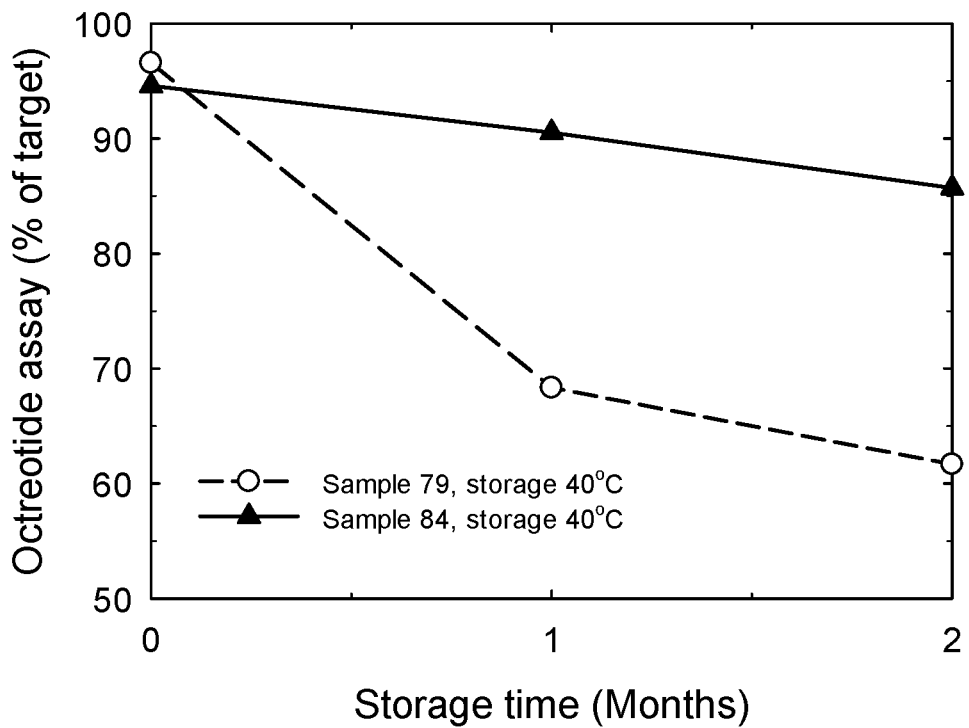

FIG. 8. OCT assay in SPC/GDO/EtOH/PG (Sample 79—reference without EDTA and Sample 84 with 100 ppm EDTA) based formulations as a function of time at 40° C./75% RH. Formulations were stored in vials with normal air in the headspace.

Figure 9:
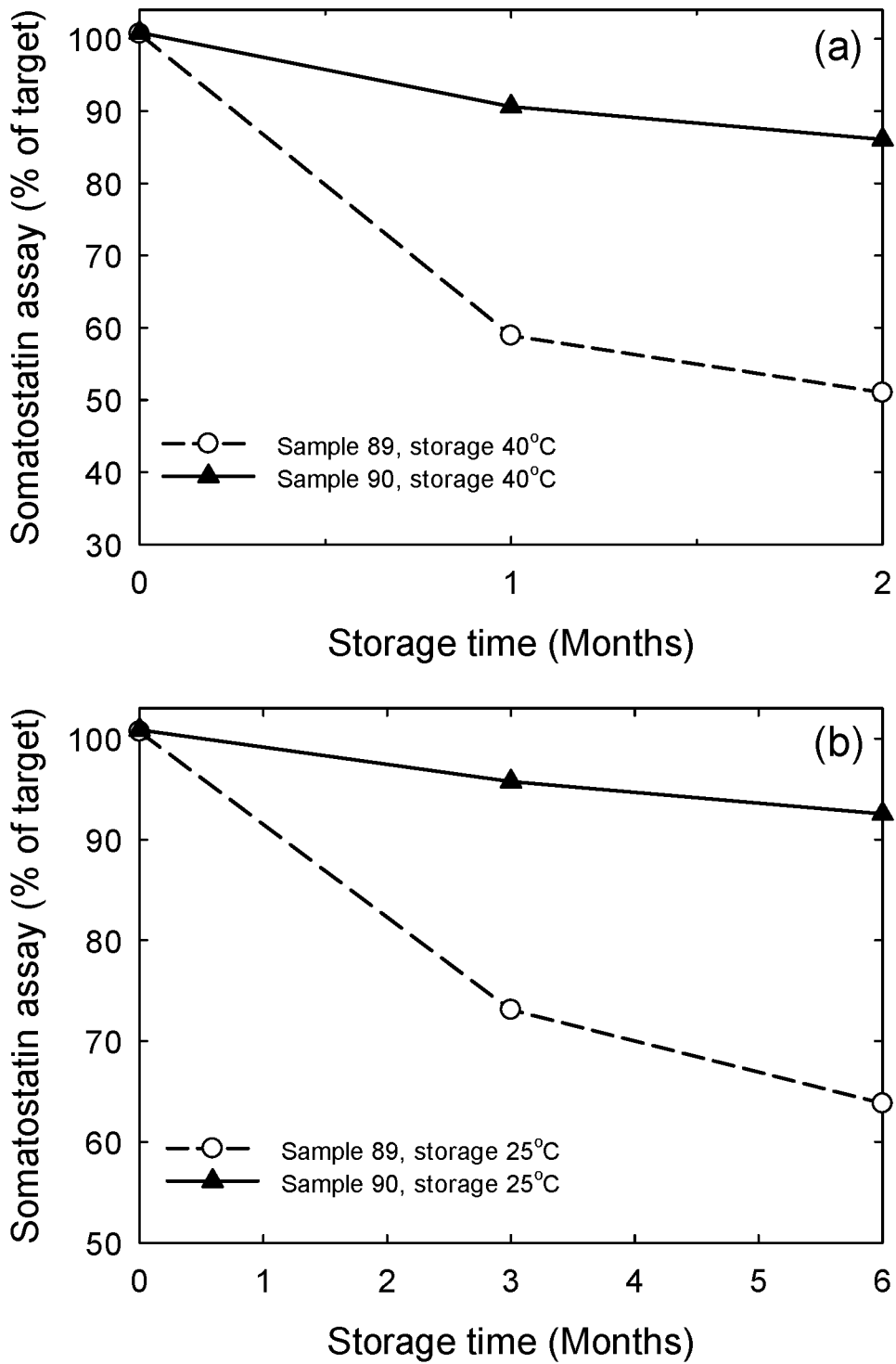

FIG. 9. SOM assay in SPC/GDO/EtOH/PG (Sample 89—reference without EDTA and Sample 90 with 100 ppm EDTA) based formulations as a function of time at 40° C./75% RH (a) and 25° C./60% RH (b). Formulations were stored in vials with normal air in the headspace.

Figure 10:
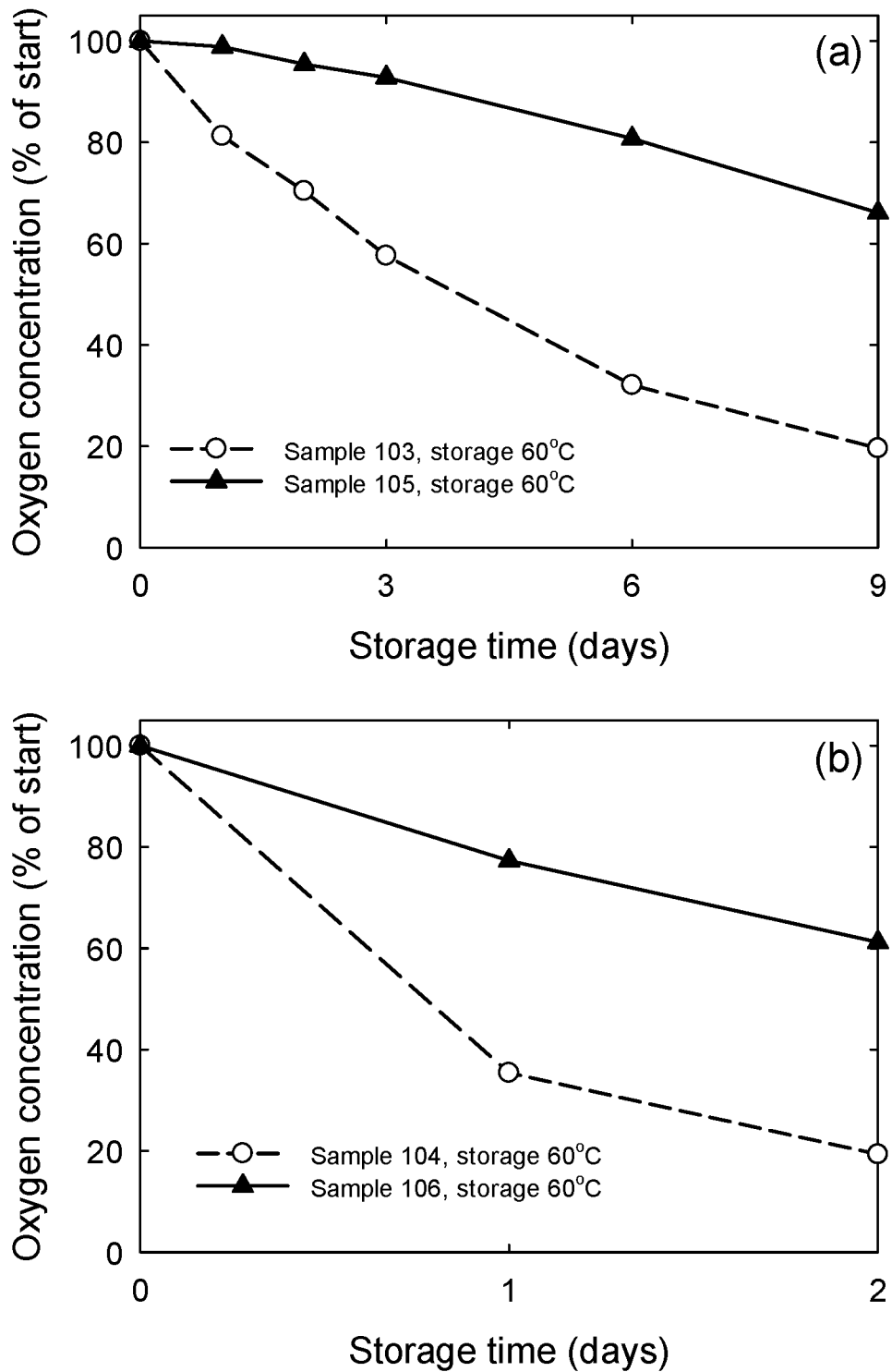

FIG. 10. Vial headspace oxygen concentration for SPC/GDO (50/50 w/w) based formulations without (Samples 103 and 104) and with 100 ppm EDTA (105 and 106) in the absence (a) and presence of 5 ppm $Fe^{3+}$ (b) as a function of time at 60° C./ambient RH. Formulations were stored in vials with normal air in the headspace.

Figure 11:
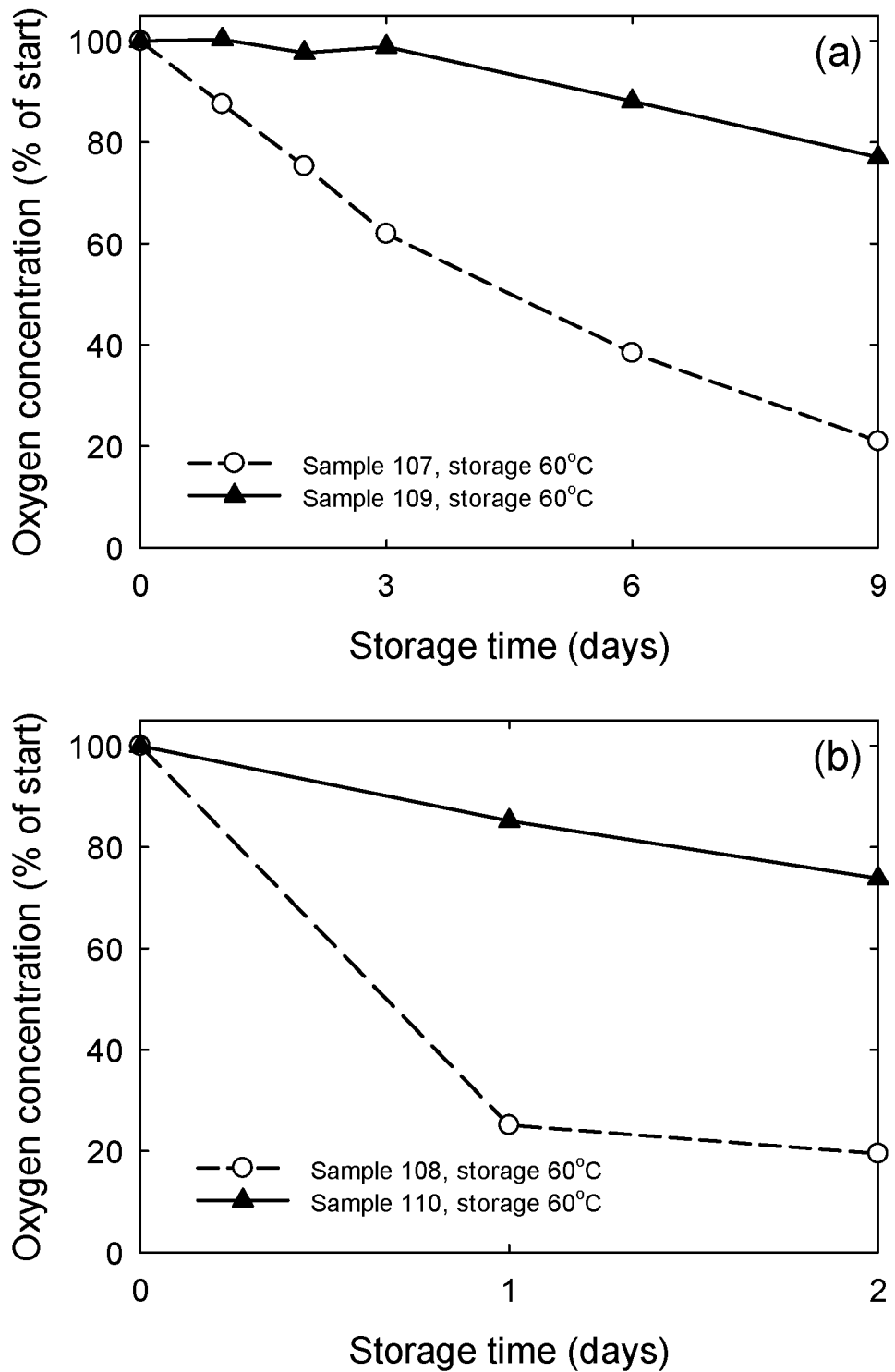

FIG. 11. Vial headspace oxygen concentration for SPC/GDO (35/65 w/w) based formulations without (Samples 107 and 108) and with 100 ppm EDTA (109 and 110) in the absence (a) and presence of 5 ppm $Fe^{3+}$ (b) as a function of time at 60° C./ambient RH. Formulations were stored in vials with normal air in the headspace.

Figure 12:
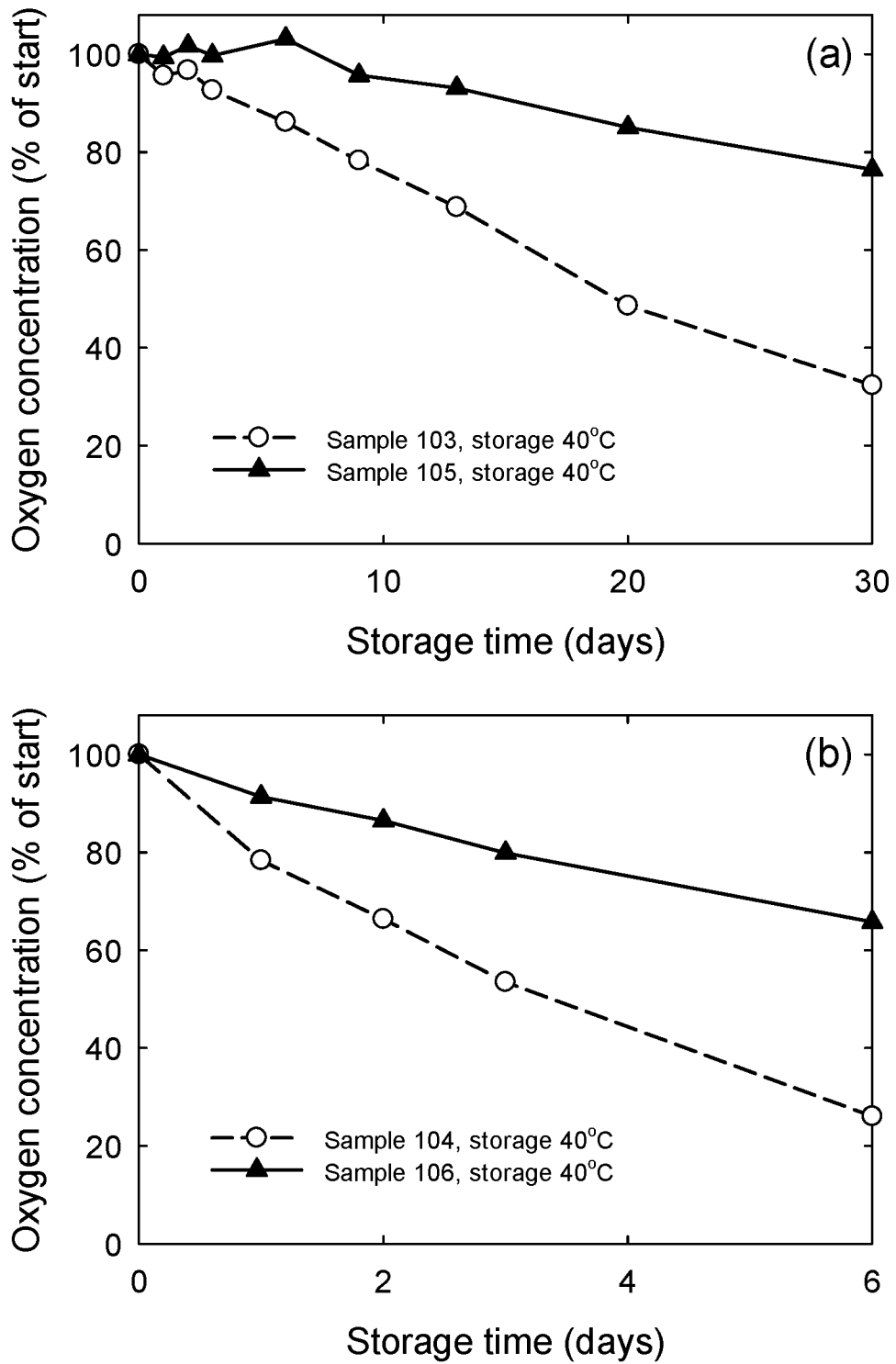

FIG. 12. Vial headspace oxygen concentration for SPC/GDO (50/50 w/w) based formulations without (Samples 103 and 104) and with 100 ppm EDTA (105 and 106) in the absence (a) and presence of 5 ppm $Fe^{3+}$ (b) as a function of time at 40° C./75% RH. Formulations were stored in vials with normal air in the headspace.

Figure 13:
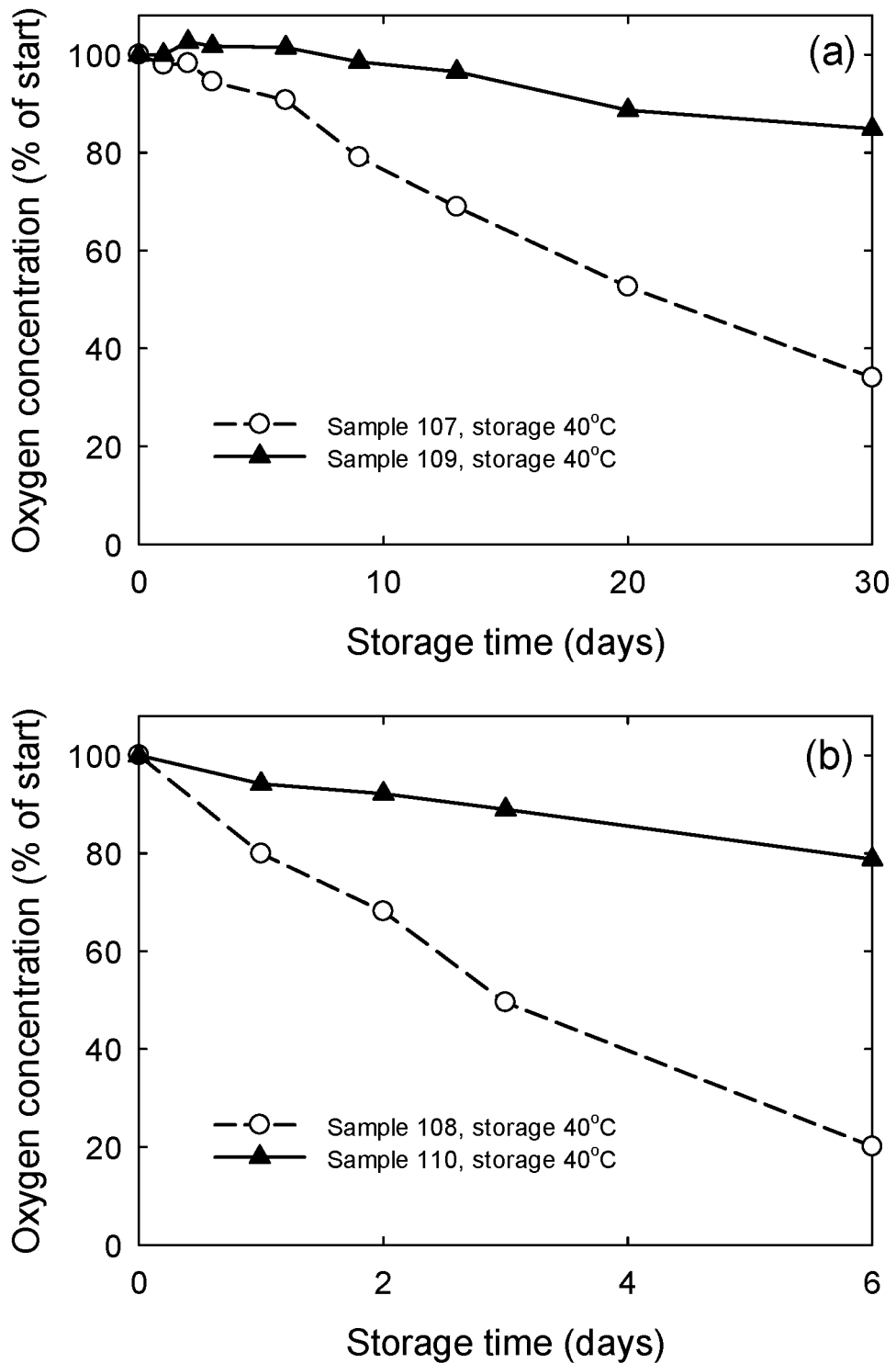

FIG. 13. Vial headspace oxygen concentration for SPC/GDO (35/65 w/w) based formulations without (Samples 107 and 108) and with 100 ppm EDTA (109 and 110) in the absence (a) and presence of 5 ppm $Fe^{3+}$ (b) as a function of time at 40° C./75% RH. Formulations were stored in vials with normal air in the headspace.

DETAILED DESCRIPTION OF THE INVENTION

The formulations of the present invention are lipid-based, are substantially non-aqueous and form a depot composition upon contact with an aqueous fluid. As used herein, the terms "formulation" or "pre-formulation" relate to the mixture of components (a), (b), (c), (d) and (e) which is typically of low viscosity. The term "depot" relates to the composition which is formed upon exposure of the pre-formulation to excess aqueous fluid, e.g. as occurs during numerous parenteral administration routes. Without wishing to be bound by theory, it is thought that this change is brought about at least in part by exchange of solvent (c) for aqueous fluid. The depot typically has a much higher viscosity than the corresponding formulation and provides for the gradual release of any active agent contained within the depot.

In a preferred aspect, the formulations of the present invention generate a non-lamellar phase (e.g. non-lamellar liquid crystalline phase) following administration. The use of non-lamellar phase structures (such as liquid crystalline phases) in the delivery of bioactive agents is now relatively well established. A most effective lipid depot system is described in WO2005/117830, and a suitable lipid matrix for use in the present invention is described in that document, the full disclosure of which is hereby incorporated herein by reference. For a description of the most favourable phase structures of such formulations, attention is drawn to the discussion in WO2005/117830 and particularly to page 29 thereof. Preferably the pre-formulation according to the invention has an $L_2$ phase (liquid phase) structure or is a liquid solution or molecular solution.

All % are specified by weight herein throughout, unless otherwise indicated. Percent (%) by weight may be abbreviated e.g. as wt %. Furthermore, the % by weight indicated is the % of the total pre-formulation including all of the components indicated herein, unless otherwise indicated. Where a percentage by weight is given in relation to component (e) the weight relates to the amount of free base (e.g. where a salt is used), unless otherwise indicated. In certain Examples, the wt % of a specified salt is provided but is indicated where appropriate and may be readily converted to the corresponding weight of free base.

The pre-formulations can optionally consist of essentially only the components indicated herein (including where appropriate additional optional components indicated herein below and in the attached claims) and in one aspect consist entirely of such components.

The lipid-based systems described herein comprise lipid components (a) and (b), an organic solvent (c), an alkylammonium EDTA salt (d), and a somatostatin receptor agonist (e).

The present inventors have now surprisingly established that by appropriate choice of antioxidant, the oxidation resistance of the lipid and any somatostatin receptor agonist (s) contained in the pre-formulation can be significantly improved.

Whilst various alkylammonium EDTA salts are known, for instance from Scott and Kyffin (*Biochem. J* (1978) 169, 697-701), their use as an antioxidant in lipid systems and compatibility with such formulations has been hitherto unknown. Scott and Kyffin describe the use of soluble EDTA salts in the demineralisation of bone samples, where EDTA acts as a sequestering agent. A particularly suitable solution is said to be 80% aqueous ethanol containing 0.2 M trimethylammonium EDTA. No use in lipid formulations nor solubility in lipids is suggested. The purpose of the EDTA salt in the present invention is as a preservative or stability enhancing agent in lipid formulations, and is very different from that described previously.

Component a)—Neutral Lipid

Preferable ranges for component a) are 20-90 wt. %, preferably 30-70 wt. %, more preferably 33-60%, particularly 38 to 43%.

Component "a" as indicated herein is at least one di-acyl lipid (e.g. at least one neutral di-acyl lipid (having no net charge at physiological pH)) comprising a polar "head" group and two non-polar "tail" groups.

As used herein, the term "acyl lipid" relates to a lipid component containing a polyol "head" group and one or more apolar "tail groups". In certain embodiments the polyol may be glycerol, a sugar or a hexitan such as sorbitan. The term "hexitan" denotes a hexitol of formula $HOCH_2(CHOH)_4CH_2OH$ which has cyclised by formally losing one equivalent of water, to form a five or six membered ring, preferably a five membered furanose ring. Sorbitan is a particularly suitable "head group", particularly as a component of a mono-acyl lipid component.

In the case of di-acyl lipids, it is most preferred that the lipid component comprises a glycerol head group with two apolar tail groups. The two non-polar groups may have the same or a differing number of carbon atoms and may each independently be saturated or unsaturated. Examples of non-polar groups include $C_6$-$C_{32}$ alkyl and alkenyl groups, which are typically present as the esters of long chain carboxylic acids. These are often described by reference to the number of carbon atoms and the number of unsaturations in the carbon chain. Thus, CX:Z indicates a hydrocarbon chain having X carbon atoms and Z unsaturations. Examples particularly include lauroyl (C12:0), myristoyl (C14:0), palmitoyl (C16:0), phytanoyl (C16:0), palmitoleoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) and lignoceroyl (C24:9) groups. Thus, typical non-polar chains are based on the fatty acids of natural ester lipids, including caproic, caprylic, capric, lauric, myristic, palmitic, phytanic, palmitolic, stearic, oleic, elaidic, linoleic, linolenic, arachidonic, behenic or lignoceric acids, or the corresponding alcohols. Preferable non-polar chains are palmitic, stearic, oleic and linoleic acids, particularly oleic acid.

Mixtures of any number of diacyl lipids may be used as component a). Preferably this component will include at least a portion of C18 lipids (e.g. a diacyl glycerol (DAG) having one or more C18:0, C18:1, C18:2 or C18:3 non-polar groups), such as glycerol dioleate (GDO) and/or glycerol dilinoleate (GDL). A highly preferred example is DAG comprising at least 50%, preferably at least 80% and even comprising substantially 100% GDO.

Since GDO and other diacyl glycerols may be derived from natural sources, there is generally a certain proportion of "contaminant" lipid having other chain lengths etc. In this context, "pure" GDO is a di-ester of glycerol and two C18:1 fatty acids. Any other diacyl glycerol is considered to be an impurity. In one aspect, GDO as used herein is thus used to indicate any commercial grade of GDO with concomitant impurities (i.e. GDO of commercial purity). These impurities may be separated and removed by purification but providing the grade is consistent this is rarely necessary. If necessary, however, "GDO" may be essentially chemically pure GDO, such as at least 70% pure, preferably at least 75% pure and more preferably at least 80% pure GDO. Correspondingly, the C18:1 content of GDO referred to herein may be around 80%, preferably at least 85% and more preferably at least 90%.

It will be appreciated that any material used, including component a), may potentially include unavoidable trace impurities of metals, optionally including heavy metals. According to the certificates of analysis for commercially available GDO (e.g. from Croda), a typical maximum concentration of heavy metals (or elemental impurities) in GDO is 5 ppm. Without being bound by theory, the common presence of these metal components and their sequestration in the various aspects of the present invention may be at least partially responsible for the additional stability observed. However, a more common issue may be the presence of iron ions, which may be absorbed from iron-based alloy materials used in handling/storage of the materials.

Component b)—Phospholipid

Component b) in the preferred lipid matrices of the present invention is at least one phospholipid. Preferable ranges of component b) are 20-80 wt. %, preferably 30-70 wt. %, more preferably 33-55% (e.g. 35-55%), particularly 38 to 43%. Ratios of a:b are typically 40:60 to 70:30, preferably 45:55 to 55:45 and more preferably 40:60 to 54:46, such as 45:55 to 54:46 or 47:53 to 53:47. Ratios of around 50:50 (e.g. 49:51 to 51:49) are highly effective in certain embodiments.

Preferred phospholipid polar "head" groups include phosphatidylcholine, phosphatidylethanolamine, phosphatidylserine and phosphatidylinositol. Most preferred are phosphatidyl choline (PC) and phosphatidyl ethanolamine (PE), especially PC. As with component a), this component comprises a polar head group and non-polar tail group(s). The difference between components a) and b) lies principally in the polar group. The non-polar portions may thus suitably be derived from the fatty acids or corresponding alcohols considered above for component a). The phospholipid will contain two non-polar groups. Again, C18 groups are preferred and may be combined with any other suitable non-polar group, particularly C16 groups.

The phospholipid portion may be derived from a natural source. In the case of PC, suitable sources of phospholipids include egg, heart (e.g. bovine), brain, liver (e.g. bovine) and plant sources including soybean. Such sources may provide one or more constituents of component b, which may comprise any mixture of phospholipids. Any single PC or mixture of PCs from these or other sources may be used, but mixtures comprising soy PC or egg PC are highly suitable. The PC component preferably contains at least 50% soy PC or egg PC, more preferably at least 75% soy PC or egg PC and most preferably essentially pure soy PC or egg PC.

In one embodiment applicable to all aspects of the invention, component b) comprises PC. Preferably the PC is derived from soy. Preferably the PC comprises 18:2 fatty acids as the primary fatty acid component with 16:0 and/or 18:1 as the secondary fatty acid components. These are preferably present in the PC at a ratio of between 1.5:1 and 6:1. PC having approximately 60-65% 18:2, 10 to 20% 16:0, 5-15% 18:1, with the balance predominantly other 16 carbon and 18 carbon fatty acids is preferred and is typical of soy PC.

In an alternative but equally preferred embodiment, the PC component may comprise synthetic dioleoyl PC (DOPC). The use of DOPC may provide increased stability and so will be particularly preferable for compositions needing to be stable to long term storage, and/or having a long release period in vivo. In this embodiment the PC component preferably contains at least 50% synthetic dioleoyl PC, more preferably at least 75% synthetic dioleoyl PC and most preferably essentially pure synthetic dioleoyl PC. Any remaining PC is preferably soy or egg PC as above.

Since the pre-formulations of the invention are to be administered to a subject it is important that the components are biocompatible. In this regard, the preferred lipid matrices for use in the pre-formulations of the present invention are highly advantageous since PC and diacyl glycerols are well tolerated and are broken down in vivo into components that are naturally present in the mammalian body.

It will be appreciated that component b) may include unavoidable trace impurities of heavy metals. According to the certificates of analysis for commercially available soy PC (e.g. from Lipoid), a typical maximum concentration of heavy metals (or elemental impurities) in soy PC is 10 ppm.

Synthetic or highly purified PCs, such as dioleoyl phosphatidyl choline (DOPC) are highly appropriate as all or part of component b). The synthetic dioleoyl PC is most preferably 1,2-dioleoyl-sn-glycero-3-phosphocholine, and other synthetic PC components include DDPC (1,2-Didecanoyl-sn-glycero-3-phosphocholine); DEPC (1,2-Dierucoyl-sn-glycero-3-phosphocholine); DLOPC (1,2-Dilinoleoyl-sn-glycero-3-phosphocholine); DLPC (1,2-Dilauroyl-sn-glycero-3-phosphocholine); DMPC (1,2-Dimyristoyl-sn-glycero-3-phosphocholine); DOPC (1,2-Dioleoyl-sn-glycero-3-phosphocholine); DPPC (1,2-Dipalmitoyl-sn-glycero-3-phosphocholine); DSPC (1,2-Distearoyl-sn-glycero-3-phosphocholine); MPPC (1-Myristoyl-2-palmitoyl-sn-glycero 3-phosphocholine); MSPC (1-Myristoyl-2-stearoyl-sn-glycero-3-phosphocholine); PMPC (1-Palmitoyl-2-myristoyl-sn-glycero-3-phosphocholine); POPC (1-Palmitoyl-2-oleoyl-sn-glycero-3-phosphocholine); PSPC (1-Palmitoyl-2-stearoyl-sn-glycero-3-phosphocholine); SMPC (1-Stearoyl-2-myristoyl-sn-glycero-3-phosphocholine); SOPC (1-Stearoyl-2-oleoyl-sn-glycero-3-phosphocholine); and SPPC (1-Stearoyl-2-palmitoyl-sn-glycero-3-phosphocholine), or any combination thereof.

A particularly favoured combination of components a) and b) are GDO with PC, especially GDO with soy PC and/or DOPC. Appropriate amounts of each component suitable for the combination are those amounts indicated herein for the individual components in any combination. This applies also to any combinations of components indicated herein, where context allows.

Component c)—Biocompatible Organic Solvent

Component c) of the pre-formulations of the invention is at least one biocompatible organic solvent. Since the pre-formulation is to generate a depot composition following administration (e.g. in vivo), typically upon contact with excess aqueous fluid, it is desirable that this solvent be tolerable to the subject and be capable of mixing with the aqueous fluid, and/or diffusing or dissolving out of the pre-formulation into the aqueous fluid. Solvents having at least moderate water solubility are thus preferred. As will be described hereinafter, component c) may include a polar co-solvent.

Component c) comprises or consists of at least one solvent selected from the group consisting of: alcohols, amines, amides or esters. Preferably component c) comprises at least a mono-alcoholic solvent. Most preferably component c) comprises ethanol, propanol, ispropanol, or mixtures thereof. It is particularly preferred the component c) comprises or consists of ethanol. Component c) may comprise or consist of a mono-alcoholic solvent, preferably ethanol, and a polar co-solvent. Mixtures comprising or consisting of ethanol and propylene glycol are also highly preferred.

The amount of component c) in the pre-formulation will have a considerable effect upon several features. In particular, the viscosity and the rate (and duration) of release may alter significantly with the solvent level. The amount of solvent will thus be at least sufficient to provide a low viscosity mixture but will additionally be determined so as to provide the desired release rate. Typically a level of 1 to 30%, particularly 2 to 20% solvent will provide suitable release and viscosity properties. In some embodiments, levels of 2 to 18%, such as 2 to 16%, especially 2 to 15% are preferred. In particularly preferred embodiments the amount of c) is 5 to 18%, such as 8 to 18%, such as 9 to 17%, especially 11 to 15%.

As indicated above, the amount of component c) in the pre-formulations of the invention will be at least sufficient to provide a low viscosity mixture (e.g. a molecular solution) of components a) to e), and will be easily determined for any particular combination of components by standard methods.

The phase behaviour may be analysed by techniques such as visual observation in combination with polarized light microscopy, X-ray scattering and diffraction techniques, nuclear magnetic resonance, and cryo-transmission electron microscopy (cryo-TEM) to look for solutions, $L_2$ or $L_3$ phases, or liquid crystalline phases or as in the case of cryoTEM, dispersed fragments of such phases. Viscosity may be measured directly by standard means. As described above, an appropriate practical viscosity is that which can effectively be syringed and particularly sterile filtered. This will be assessed easily as indicated herein.

A highly preferred combination for components a), b) and c) is GDO, soy PC and ethanol, especially GDO, soy PC and mixtures of ethanol and propylene glycol. As indicated above, appropriate amounts of each component suitable for the combination are those amounts indicated herein for the individual components, in any combination.

It is preferable that little or none of component c) contains halogen substituted hydrocarbons since these tend to have lower biocompatibility.

Component c) as used herein may be a single solvent or a mixture of suitable solvents but will generally be of low viscosity. The viscosity of the "low viscosity" solvent component c) (single solvent or mixture) should typically be no more than 18 mPas at 20° C. This is preferably no more than 15 mPas, more preferably no more than 10 mPas and most preferably no more than 7 mPas at 20° C.

It is described in WO2012/160213 that the addition of a polar solvent in addition to a mono-alcoholic solvent results in numerous advantages including reduced viscosity and reduced active agent burst profile. In addition to the preferred aspects described previously for component c), in one particularly preferred embodiment component c) comprises a mono-alcoholic solvent and a polar co-solvent. The term "polar co-solvent" as used herein defines a solvent having a dielectric constant (diel) of at least 28 at 25° C., more preferably at least 30 at 25° C. but is not water or any aqueous fluid. Highly suitable examples include propylene glycol (diel ~32), and N-methyl-2-pyrrolidone (NMP, diel~32). The preferred levels of component c) recited herein apply equally to mixtures of mono-alcoholic solvent and a polar co-solvent unless context permits otherwise.

In a particularly preferred embodiment component c) comprises, consists essentially of, or consists of a mixture of a mono-alcoholic solvent and a polar co-solvent. The polar co-solvent may in one embodiment be a di-alcoholic C3-C6 organic solvent, i.e. a C3-C6 organic solvent comprising two hydroxy groups. The di-alcoholic solvent is preferably propylene glycol. When present, a polar co-solvent is included at a level of 2 to 12 wt. % of the pre-formulation, such as 3 to 10 wt. %, especially 4 to 9 wt. %. This level is counted as part of the ranges recited above for component c). Most preferably component c) comprises, consists essentially of, or consists of a mixture of ethanol and propylene glycol (PG).

Where both an organic mono-alcoholic solvent and a polar co-solvent are present, e.g. ethanol and PG, the ratio of mono-alcoholic solvent to polar co-solvent solvent is preferably in the range 20:80 to 70:30, preferably 30:70 to 70:30 (w/w), more preferably 40:60 to 60:40. Approximately equal amounts of mono- and di-alcoholic components are highly appropriate.

In an especially preferred embodiment component c) is present at a level of 1 to 30% and comprises, consists or consists essentially of a mixture of ethanol and PG, wherein the ratio of ethanol to PG (w/w) is in the range of 30:70 to 70:30, preferably 40:60 to 60:40. More preferably component c) is present at a range of 5 to 15 wt % or 8 to 18 wt %, most preferably 8-18% wt %, and is a mixture of ethanol and PG in a ratio of 40:60 to 60:40 (w/w).

For the avoidance of doubt, even where a polar co-solvent is present in the pre-formulations of the present invention, the total water level will remain as described in the various embodiments herein (e.g. 0.1 to 1.0 wt %).

Component d)—Alkylammonium Salt

Component d) is an alkylammonium salt comprising an anion of EDTA ("ethylenediamine tetraacetic acid" or "edetic acid") or an anion of an EDTA analogue as described below, and at least one alkylammonium cation of Formula (I):

$$NR^1R^2R^3R^{4n+} \qquad (I)$$

wherein each $R^1$-$R^4$ is independently H, or a linear or branched C1-10 group (as described herein), with the proviso that at least one of $R^1$-$R^4$ is not H.

Typically, and preferably, n=1. However, for ammonium salts containing more than one nitrogen atom, such as ethylenediamine ($NH_2CH_2CH_2NH_2$) it may be possible for a mixture of +1 and +2 cations to exist (i.e. $NH_2CH_2CH_2NH_3^+$ and $NH_3CH_2CH_2NH_3^{2+}$). To a certain extent the formation of polycationic species may be prevented by providing an excess of the precursor amine as described below. However, the person skilled in the art will appreciate when the formation of mixed cations is a possibility.

Each of $R^1$ to $R^4$ may be the same or different, with the proviso that at least one of $R^1$ to $R^4$ is not H. Preferably all of the substituent groups $R^1$ to $R^4$ which are not H are the same. Preferred cations are therefore $NRH_3^+$, $NR_2H_2^+$ and $NR_3H^+$ or $NR_4^+$ wherein the "R" groups in each are the same. Primary, secondary and tertiary ammonium cations are preferred to quaternary cations as the former can be easily prepared by combining the appropriate amine with EDTA as described below.

Each of $R^1$ to $R^4$ is independently H or a linear or branched C1-10 alkyl, alkenyl or alkynyl group, preferably C1-C5. Most preferably each of $R^1$ to $R^4$ is a linear or branched C1-5 alkyl group, especially a linear C1-C5 or C1-C3 alkyl group.

Each $R^1$ to $R^4$ may independently be further substituted with one or more OH or $NH_2$ (or $NH_3^+$) groups. In an embodiment, for a substituent R containing m carbon atoms, the substituent may contain a maximum of m-1 OH and/or NH₂ groups per substituent. For instance, if R1 is C8 then R1 may contain up to 7 OH groups, especially one OH unit attached to each carbon atom other than the carbon atom directly joined to the ammonium N atom. This embodiment is of particular relevance to the case in which the alkylammonium cation is derived from an aminopolyol (e.g. meglumine (MeNHCH₂(CHOH)₄CH₂OH)). As an alternative example, if R1 is C3 then R1 may contain up to 2 OH groups, such as serinol (NH₂CH(CH₂OH)₂). In an embodiment at least one of R¹-R⁴ is a linear C1-C6 group substituted with at least one OH or NH₂ group.

In one embodiment any two of the groups R1 to R4 taken together form a C4-C8, preferably C4-C6 ring, which may optionally contain one or more exocyclic OH or NH2 groups. If any two of the groups R¹ to R⁴ together form a ring then a single endocyclic O or NH unit may also be present. In particular, it is envisaged that morpholine salts may be used (i.e. if any two of R¹ to R⁴ together form a six-membered C4 ring containing one endocyclic O atom). In this embodiment two of the groups R¹ to R⁴ along with N together form a morpholine ring, while the remaining groups R¹ to R⁴ have the definition above.

Particularly preferred alkylammonium cations include those derived from N-protonation, or in a less preferred embodiment N-alkylation, of an amine selected from:
Ethanolamine "ETA" (NH₂(CH₂CH₂OH));
Diethanolamine "DiETA" (NH(CH₂CH₂OH)₂);
meglumine (NH(CH₃)CH₂(CHOH)₄CH₂OH));
tris-hydroxymethylamine "TRIS" (N(CH₂OH)₃);
ethylenediamine (NH₂CH₂CH₂NH₂); or
serinol (NH₂CH(CH₂OH)₂).

It is preferred that the mass of the alkylammonium cation of Formula (I) is below 500 amu, preferably below 350, especially below 250 amu. Salts of EDTA containing the ethanolammonium ion (HOCH₂CH₂NH₃⁺) are particularly preferred in the invention. It is most preferred that the EDTA salt is a salt of EDTA with ethanolamine (ETA), preferably EDTA with ETA only.

The alkylammonium cation is thought to aid in increasing the lipid solubility the EDTA salt relative to a conventional metal (inorganic) EDTA salt such as disodium EDTA. As EDTA contains four carboxylic acid units the alkylammonium salt may comprise up to four ammonium cations and a tetraanionic EDTA anion.

As used herein, the term "EDTA" may represent ethylenediaminetetraacetic acid as such. Alternatively, EDTA as indicated herein may include both ethylenediaminetetraacetic acid itself and EDTA analogues. "EDTA" herein thus includes "EDTA and analogues thereof" whenever context allows. Suitable EDTA analogues are those containing at least one glycinate unit (i.e. the unit —NCH₂COO—) within the molecule, preferably at least 2, at least 3 or at least 4 glycinate units. Suitable EDTA analogues include:
Iminodiacetic acid (IDA)—(NH(CH₂CO₂H)₂;
Nitrilotriacetic acid (NTA)—N(CH₂CO₂H)₃;
Pentetic acid*—N(CH₂CO₂H)₂CH₂CH₂N(CH₂CO₂H)CH₂CH₂N(CH₂CO₂H)₂;
Egtazic acid—N(CH₂CO₂H)₂CH₂CH₂OCH₂CH₂OCH₂CH₂N(CH₂CO₂H)₂
NOTA—[N(CH₂CO₂H)CH₂CH₂]₄
DOTA—[N(CH₂CO₂H)CH₂CH₂]₄
*Also known as "DTPA"

In an embodiment the EDTA analogue has the structure indicated in Formula (II) below:

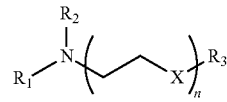

EDTA analogue - Formula (II)

wherein n is 1-10, preferably 1-5, especially 1, 2 or 3;
wherein X is CH₂, O or NR₄
wherein R₁, R₂, R₃ and R₄ are each individually H or CH₂CO₂H, preferably CH₂CO₂H; or
wherein R₁ and R₃ together represent a covalent bond (i.e. the EDTA analogue is cyclic) and R₂ and R₄ are each individually H or CH₂CO₂H, preferably CH₂CO₂H.

Amounts of EDTA and ratios of EDTA to (e) defined herein apply equally to EDTA and EDTA analogues. In all embodiments it is preferred that EDTA is used as the counterion in component (d).

Formation of EDTA Salt

The EDTA salt may be pre-formed and dissolved or dispersed in one or more of the components prior to forming the pre-formulation, or may be formed in situ. In situ formation is generally preferred for simplicity of operation. A suitable method for preparing the alkylammonium EDTA salt involves dissolving EDTA (acid form) and the requisite alkylamine (base) in the solvent component (c), or in a solvent which is a precursor to (or sub-component of) the solvent component (c), and providing mixing until the solids are fully dissolved.

The inventors have established that as a general rule, for a mono-amine at least 3.0, preferably at least 3.5 (e.g. 3.5 to 10) molar equivalents of amine (which is a precursor to the ammonium salt) are required relative to the amount of EDTA in order to solubilize the salt in the solvent component (c). As is described in the examples, the minimum ratio between the amine and EDTA necessary to solubilize the salt varies depending on the specific choice of alkylammonium salt. However, an appropriate molar ratio can be achieved by experimentation by simply observing at what molar excess of alkylamine the solid EDTA fully dissolves in the solvent. In an embodiment, a greater than stoichiometric ratio of amine is added than is formally needed to form the tetraammonium EDTA salt. For instance, as is described in the following examples, efficient solubilisation of EDTA using TRIS may require 5.0 or more equivalents of amine.

For certain di-amines or tri-amines the molar ratio to achieve adequate EDTA salt solubility may not be as high as for a mono-amine. For polyamines (diamines, triamines etc), such as NH₂CH₂CH₂NH₂, the required molar ratio may be lower than that for a mono-amine. Suitable levels for polyamines may be 2.0 or more (e.g. 2.0 to 4.0), or 2.5 or more. Again, suitable levels can be found by optimisation. As a guide, the molar equivalents of amine discussed above may represent the molar ratio of mono-amine to EDTA or the ratio of amine moieties to EDTA where the amine (or mixture of amines) has more than one amine moiety in the molecule (either individually or on average for a mixture).

There is no upper limit on the number of equivalents of amine which may be present, although it will be appreciated that typically no more amine should be included than is necessary to ensure efficient solubilisation. A typical practical limit may be 20 equivalents, preferably 10 equivalents.

The inventors have established that in order to form the alkylammonium EDTA salt, it is necessary to begin with the acid form of EDTA rather than the commonly used disodium EDTA (EDTA(Na)). Neither EDTA (edetic acid) nor EDTA (Na) are soluble in suitable/preferred solvents (e.g. EtOH/PG) without an alkylamine (e.g. ETA), even after several months of mixing. Surprisingly, EDTA(Na) is insoluble in EtOH/PG even in the presence of ETA.

A typical procedure for producing the salt therefore involves dissolving the free tetraacid EDTA (which may be a hydrate) in the solvent (c), or in a solvent which is a precursor to the solvent component (c), which comprises at least a mono-alcoholic solvent such as ethanol, and may also comprise a polar co-solvent as previously described, preferably in a mixture of ethanol and PG. The requisite number of equivalents of alkylamine are then added and the mixture is agitated, e.g. by end-over-end rotation or magnetic stirring, until the EDTA is dissolved, as can be established by visual observation. 24 h of mixing is usually adequate to ensure efficient solubility, e.g. in the case of the formation of an ETA/EDTA salt.

It is also within the scope of the invention to form the salt in a solvent which is a precursor to the solvent component (c). By "precursor" it is meant that the solvent in which the EDTA salt is formed is not identical to the final composition of solvent component (c), but that the content of solvent(s) in the precursor can be adjusted to arrive at the final composition of the solvent (c) in the pre-formulation. As an example, the salt may be formed in a mixture of EtOH:PG (1:2) and additional ethanol added during or after salt formation in order to reach a final composition of EtOH:PG (1:1) for component (c).

Ratio of Alkylamine to EDTA

The inventors have surprisingly established that above a certain ratio of alkylamine:EDTA the chemical stability of the active agent in the pre-formulation begins to decrease. This may be a result of reaction between the excess alkylamine and the active agent, either directly or via degradation products. Accordingly, it is preferred that the amount of alkylamine chosen is sufficient to fully solubilize all of the EDTA in the solvent component (c) but is not significantly beyond this level. It is preferred that the amount of alkylamine included is no more than 2 times the required level to achieve complete solubility, preferably no more than 1.5 times, preferably no more than 1.2 times. The amount of alkylamine necessary to fully solubilize ETDA in the solvent component (c) can be established by the methods described previously.

In an embodiment component (d) comprises an alkylammonium counterion having only one amino or alkylamino group and the ratio of EDTA: the total of said alkylammonium counterion and any amine free base thereof in the pre-formulation is 1:≥3.0; preferably 1:≥3.5, most preferably in the range of 1:3.0 to 1:10.

In an embodiment component (d) comprises an alkylammonium counterion having two or more amino and/or alkylamino groups, wherein the ratio of EDTA: the total of said alkylammonium counterion and any amine free base thereof in the pre-formulation is 1:≥2.0; preferably in the range of 1:2.0 to 1:4.0.

In a particularly preferred aspect the EDTA salt is an ETA salt of EDTA. The inventors have established that in this embodiment in order to fully solubilise EDTA in the solvent component (c) (e.g. a mixture of EtOH/PG 50:50) it is necessary to include around at least 3.5 molar equivalents of ETA relative to the amount of EDTA. Accordingly, the amount of ETA to EDTA is preferably no more than 7:1. The equivalents of ETA to EDTA are preferably in the range of 3.5 to 7 (mol/mol), preferably 3.5 to 5, most preferably 3.5 to 4.5. Most preferably 4 equivalents of ETA are used relative to the amount of EDTA (mol/mol).

Amount of EDTA Salt

The level of alkylammonium EDTA salt is chosen to ensure appropriate stability of the components of the lipid vehicle and active agent for the storage duration required and under the chosen storage conditions. Factors to be considered when determining appropriate amounts of alkylammonium EDTA salt include: the reactivity of the lipid components and active agent, the loading of active agent, the molecular mass of the active agent, storage conditions (oxygen content, humidity, temperature), the duration of oxidative protection required and the concentration of metal ions present in the pre-formulation (which may catalyse decomposition processes).

In order to suppress the catalytic activity of metals, e.g. Fe, the pre-formulation will typically include the EDTA salt at a level such that the ratio of EDTA salt to metal (e.g Fe, especially in the form of Fe(II) and Fe(III) ions) is at least around 2:1 (mol/mol), i.e. the EDTA salt is present in at least a 2 times molar excess. In a typical procedure the molar ratio will be based upon the maximum estimated metal ion (especially Fe ion) concentration and EDTA provided in a ratio of around 2:1 to this maximum estimate. The result in practice will then be 2:1 or greater molar ratio of EDTA to metal (e.g. Fe) ions.

The inventors have established that there is a preferred level of EDTA, above which no advantage in terms of oxidation resistance of the formulation is observed, and indeed the stability may be somewhat reduced. This is influenced by the amount of metal ions (e.g. Fe ions) present in the formulation as is discussed in detail in the "Experimental" section. However, in general a suitable amount of EDTA salt in the pre-formulation (calculated in terms of EDTA free acid) will be 0.001-0.02 wt % (10-200 ppm), preferably 0.001-0.015 wt % (10-150 ppm), especially 0.002-0.015 wt % (20-150 ppm). A particularly preferred level is 0.005-0.015 wt. % (50-150 ppm), most preferably 0.008-0.012 wt. % (80-120 ppm). A level of 100 ppm is suitable for protecting against up to 10 ppm of metal (iron equivalents) which is reasonable for ensuring appropriate drug product robustness.

In certain embodiments, the levels of EDTA (based on the weight of EDTA alone and not including the amine countercations) may range from 0.001 to 0.8 wt % (10 to 8000 ppm), 0.002 to 0.5 wt % (20 to 5000 ppm), 0.005 to 0.2 wt % (50 to 2000 ppm) or 0.01 to 0.1 wt % (100 to 1000 ppm) of the pre-formulation. In certain embodiments the level of EDTA may range from 0.001 to 0.050 wt % of the formulation (10 to 500 ppm), preferably 0.02 to 0.30 wt % (20 to 300 ppm) of the formulation.

The level of alkylamine to be added can be established once the optimum ratio of alkylamine to EDTA is found, as described in preceding sections.

In an embodiment the ratio of (d) to (e) is in the range 1:1 to 1:5000 (w/w), preferably 1:1 to 1:500 (w/w), preferably in the range of 1:50 to 1:300.

Water Content

The inclusion of EDTA salts containing an alkylammonium ion of Formula (I) allows for an antioxidant to be included in the pre-formulation at low levels of water. It is however extremely difficult to completely eliminate all traces of water (especially from the raw materials). Even if essentially water-free formulations could be achieved, pre-formulations will typically be stored in ready-to-use form, e.g. in syringes and possibly under refrigerated conditions. Syringes are often not completely air-tight meaning that the level of water in the pre-formulation may increase to an appreciable level over time, e.g. over months, even if the initial level of water is insignificant.

The initial absolute level of water in the pre-formulation is between 0 to 1.0 wt. %. Preferably the water content is less than 1.0 wt. %, preferably less than 0.8 wt %, preferably less than 0.5 wt %. Most preferably, the level of water is in the range of 0.1 to 0.9 wt. %, especially 0.2 to 0.8 wt. %. These levels refer to the absolute level of water and not added levels of water. Any unavoidable trace of water present within components a), b) or c) is included in this stated level of water. After 3 months of storage, the absolute water level is preferably no more than 1.5 wt %. Absolute levels of water can be measured by methods well known in the art such as Karl Fischer titration. In particular, the water content is preferably measured according to the procedure in United States Pharmacopoeia (USP 40-NF 35, USP<921>Water determination, Method Ia.

Component e)—Active Agent

The pre-formulations of the present invention contain one or more somatostatin receptor agonist(s), equivalently referred to herein as "active agents". The somatostatin receptor agonist(s) may be endogenous or may be synthetic analogues.

Somatostatin receptor agonists often have a short residence time in the body due to rapid breakdown (in vivo degradation) or excretion. By administering such agents in the form of a depot composition formed from the pre-formulation of the present invention, the agents are provided at a sustained level for a length of time which may stretch to days, weeks or even several months in spite of having rapid clearance rates. This offers obvious advantages in terms of stability and patient compliance over dosing multiple times each day for the same period. In one preferred embodiment, the somatostatin receptor agonist has a biological half life (upon entry into the blood stream) of less than 1 day, preferably less than 12 hours and more preferably less than 6 hours. In some cases this may be as low as 1-3 hours or less.

The amount of somatostatin receptor agonist to be formulated with the pre-formulations of the present invention will depend upon the functional dose and the period during which the depot composition formed upon administration is to provide sustained release. Typically, the dose formulated for a particular agent will be around the equivalent of the normal daily dose multiplied by the number of days the formulation is to provide release. Evidently this amount will need to be tailored to take into account any differences in bioavailability or adverse effects of a large dose at the beginning of treatment and so this will generally be the maximum dose used. The precise amount suitable in any case will readily be determined by suitable experimentation.

A further considerable advantage of the depot compositions of the present invention is that the somatostatin receptor agonist(s) within the depot formed by the pre-formulation upon administration are released gradually over long periods without the need for repeated dosing. The pre-formulations are thus highly suitable for situations where patient compliance is difficult, unreliable or where a level dosage is highly important, such as mood-altering actives, those actives with a narrow therapeutic window, and those administered to children or to people whose lifestyle is incompatible with a reliable dosing regime and for "lifestyle" actives where the inconvenience of repeated dosing might outweigh the benefit of the active.

The active agent component e) is a somatostatin receptor agonist or mixture of somatostatin receptor agonists. Where reference is made to "somatostatin receptor agonist", it is to be understood that this also encompasses mixtures of somatostatin receptor agonists unless context permits otherwise.

Somatostatins (Growth Hormone Release Inhibiting Factors, SSTs) are natural peptide hormones with a wide distribution in animals, acting as neurotransmitters in the central nervous system, and having diverse paracrine/autocrine regulatory effects on several tissues. Two biologically active products are known in higher species, SST-14 and SST-28, the latter being a congener of SST-14 extended at the N-terminus.

SST-14 is a 14 residue cyclic peptide hormone having the sequence Ala-Gly-Cys-Lys-Asn-Phe-Phe-Trp-Lys-Thr-Phe-Thr-Ser-Cys, where the two cysteine residues are connected by a disulphide bridge to generate a type II β-turn at the key binding sequence of Phe-Trp-Lys-Thr. The biological half-life of natural SST-14 is very short (1-3 minutes) and so is in itself a challenging peptide for therapeutic use, but an increasing number of somatostatin receptor agonists are becoming available with higher activities and/or longer clearance times in vivo.

Somatostatin receptor agonists (SRAs), such as SST-14, SST-28, octreotide, lanreotide, vapreotide, pasireotide (SOM 230) and related peptides, are used or indicated in the treatment of a variety of conditions where they are typically administered over an extended period. These agonists form a preferred class of somatostatin receptor agonists for use as component e) in the present invention.

Octreotide, for example, is the synthetic octapeptide with sequence D-Phe-Cys-Phe-D-Trp-Lys-Thr-Cys-Thr-ol (2-7 disulphide bridge) and is typically administered as an acetate salt. This SST-14 derivative retains the key Phe-(D)Trp-Lys-Thr β-turn required for in vivo SST-like activity but, in contrast to the natural hormone, has a terminal half-life of around 1.7 hours. Octreotide is used in treatment of conditions including carcinoid tumours and acromegaly, and is typically administered over a sustained period of weeks, or more commonly many months or years. Somatostatin receptor agonists are of particular interest for the treatment of many different types of cancers since a wide variety of tumours are found to express somatostatin receptors (SSTRs). There are five known types of SSTRs (SSTR1-SSTR5), showing equally high affinity for SST-14. The most investigated somatostatin receptor agonists, including octreotide, show high selectivity for SSTR2 and SSTR5; thus, octreotide is of particular interest for the treatment of tumours expressing these types of receptors.

The most common "simple" formulation of Octreotide is "Sandostatin"® from Novartis. This is an aqueous solution for subcutaneous (s.c) injection, and a 100 µg dose reaches a peak concentration of 5.2 ng/ml at 0.4 hours post injection. The duration of action can be up to 12 hours but s.c. dosing is generally carried out every 8 hours. Evidently, s.c. injection 3 times daily for periods of months or years is not an ideal dosing regime.

Following a single subcutaneous dose of pasireotide, human plasma levels typically peak quickly, at around 15 minutes to 1 hour after dosing, with an initial half-life of 2-3 hours following that peak. Although clearance half-life is greater for later phases of the decline, it is clear that the Cmax/Cave for such a delivery will be rather high.

Pasireotide LAR is a long acting formulation of pasireotide which addresses some of the above issues. However, this is a polymer microparticle based system with the inherent limitations of such a system, as are known in the art and described herein above.

Carcinoid tumours are intestinal tumours arising from specialised cells with paracrine functions (APUD cells). The primary tumour is commonly in the appendix, where it is clinically benign. Secondary, metastatic, intestinal carcinoid tumours secrete excessive amounts of vasoactive substances, including serotonin, bradykinin, histamine, prostaglandins, and polypeptide hormones. The clinical result is carcinoid syndrome (a syndrome of episodic cutaneous flushing, cyanosis, abdominal cramps, and diarrhea in a patient with valvular heart disease and, less commonly, asthma and arthropathy). These tumours may grow anywhere in the gastrointestinal tract (and in the lungs) with approximately 90% in the appendix. The remainder occurs in the ileum, stomach, colon or rectum. Currently, treatment of carcinoid syndrome starts with i.v. bolus injection followed by i.v. infusion. When sufficient effect on symptoms has been established, treatment with a depot formulation of octreotide formulated in ploy lactic-co-glycolic acid (PLGA) microspheres is started. However, during the first two weeks or more after injection of the depot, daily s.c. injections with octreotide are recommended to compensate for the slow release from the PLGA spheres.

Since SST-14 is a peptide hormone, typical somatostatin receptor agonists will be peptides, especially of 14 or fewer amino acids. Preferably such peptides will be structurally constrained such as by being cyclic and/or having at least one intramolecular cross-link. Amide, ester or particularly disulphide crosslinks are highly suitable. Preferred constrained peptides will exhibit a type-2 β turn. Such a turn is present in the key region of somatostatin. Peptides may contain only amino acids selected from those 20 α-amino acids indicated in the genetic code, or more preferably may contain their isomers and other natural and non-natural amino acids, (generally α, β or γ, L- or D-amino acids) and their analogues and derivatives. The term "somatostatin receptor agonist" as used herein may optionally also encompass SST-14 and/or SST-28, since these are viable peptide actives when formulated as salts in the very high performance slow-release formulations described herein.

Amino acid derivatives and amino acids not normally used for protein synthesis are especially useful at the termini of the somatostatin receptor agonist, where the terminal amino or carboxylate group may be substituted by or with any other functional group such as hydroxy, alkoxy, ester, amide, thio, amino, alkyl amino, di- or tri-alkyl amino, alkyl (by which is meant, herein throughout $C_1$-$C_{18}$ alkyl, preferably $C_1$-$C_8$ alkyl e.g. methyl, ethyl, n-propyl, isopropyl, n-butyl, iso-, sec- or t-butyl etc.), aryl (e.g phenyl, benzyl, napthyl etc) or other functional groups, preferably with at least one heteroatom and preferably having no more than 10 atoms in total, more preferably no more than 6.

Particularly preferred somatostatin receptor agonists are constrained peptides of 6 to 10 α-amino acids, of which particular examples include octreotide, lanreotide (of sequence $NH_2$-(D)Naph-Cys-Tyr-(D)Trp-Lys-Val-Cys-Thr-$CONH_2$ and its cyclic derivative of sequence $NH_2$-(D)Naph-Cys-Tyr-(D)Phe-Lys-Val-Cys-Thr-$CONH_2$ both having a Cys-Cys intramolecular disulphide crosslink), pasireotide (aka SOM 230) and vapreotide. Most preferred are octreotide and pasireotide.

The somatostatin receptor agonist will generally be formulated as 0.1 to 12% by weight of the total formulation (based on the amount of free base). Typical values will be 0.1 to 10%, 0.5 to 9%, preferably 1 to 9%, and in some embodiments 1 to 8% or 1 to 7%. A somatostatin receptor agonist content of 2-6% is suitable in certain embodiments.

The somatostatin receptor agonist will generally be formulated in an amount of 5 to 100 mg per mL of pre-formulation, preferably 10 to 80 mg/mL. In some embodiments, particularly where the somatostatin receptor agonist comprises, consists essentially of or consists of octreotide, the level of octreotide may be 10 to 50 mg/mL, such as 10 to 30 mg/mL (e.g. 10 mg/mL, 20 mg/mL, 30 mg/mL), with a level of 15 to 25 mg/mL (e.g. 20 mg/mL) being particularly appropriate. Where the somatostatin receptor agonist comprises, consists essentially of or consists of pasireotide, the level of pasireotide may be 10 to 100 mg/mL, such as 20 to 60 mg/mL (e.g. 20 mg/mL, 40 mg/mL, 60 mg/mL).

Doses of the somatostatin receptor agonist suitable for inclusion in the formulation, and thus the volume of formulation used, will depend upon the release rate (as controlled, for example by the solvent type and amount use) and release duration, as well as the desired therapeutic level, the activity and the rate of clearance of the particular active chosen. Typically an amount of 1 to 500 mg per dose would be suitable for providing a therapeutic level for between 7 and 90 days. This will preferably be 5 to 300 mg. For octreotide, the level will typically be around 10 to 180 mg (e.g. for a 30 to 90 day duration). Preferably, the amount of octreotide will be around 0.2 to 3 mg per day between injections. Thus a depot administered every 30 days would have 6 to 90 mg or a 90 day depot have 18 to 270 mg of octreotide.

For Pasireotide, the dosage would typically be an amount of around 0.05 to 40 mg per week of depot duration, preferably 0.1 to 20 mg per week duration (e.g. 1 to 5 mg per week) for a duration of 1 to 24 weeks, preferably 2 to 16 (e.g. 3, 4, 8, 10 or 12) weeks. In an alternative embodiment the pre-formulation may be formulated for dosing weekly (e.g. every 7±1 days). A total dose of 0.05 to 250 mg of Pasireotide per dose would be suitable for providing a therapeutic level for between 7 and 168 days. This will preferably be 0.1 to 200 mg, e.g. 0.2 to 150 mg, 0.1 to 100 mg, 20 to 160 mg etc. Evidently, the stability of the active and effects on the release rate will mean that the loading to duration may not be a linear relationship. A depot administered every 30 days might have, for example 0.2 to 20 mg of Pasireotide, or a 90 day depot might have 30 to 60 mg of Pasireotide.

Where the salt of said peptide somatostatin receptor agonist is used in the formulations of the present invention, this will be a biologically tolerable salt. Suitable salts include the acetate, pamoate, chloride or bromide salts. The chloride salt is most preferred.

In a further preferred embodiment of the invention the pre-formulation comprising: a lipid controlled-release matrix comprising:
  a) at least one di-acyl lipid;
  b) at least one phospholipid;
  c) at least one biocompatible, organic solvent;
  d) an alkyl ammonium EDTA salt; and
  e) at least one somatostatin receptor agonist;
wherein the pre-formulation has a water content in the range of 0 to 1.0 wt %.

In a further preferred embodiment of the invention the pre-formulation comprises:
  a) at least one di-acyl lipid;
  b) at least one phospholipid;
  c) at least one biocompatible, organic solvent;
  d) an alkyl ammonium EDTA salt; and
  e) octreotide or a salt thereof.

In a further preferred embodiment of the invention the pre-formulation comprises:
a) GDO;
b) PC;
c) ethanol and PG;
d) an alkyl ammonium EDTA salt; and
e) octreotide or a salt thereof.

In a further preferred embodiment of the invention the pre-formulation comprises:
a) 33-43% of GDO;
b) 33-55% of PC;
c) 8-18% of a mixture of ethanol and PG;
d) 10-200 ppm of an alkyl ammonium EDTA salt, preferably and ETA salt of EDTA; and
e) 0.1-12 wt % of octreotide or a salt thereof, preferably octreotide chloride.

In a further preferred embodiment of the invention the pre-formulation comprises:
a) 33-60 wt % GDO;
b) 33-55 wt % SPC;
c) 2-20 wt % EtOH and PG;
d) 0.001-0.050 wt % EDTA;
e) 1-10 wt % OCT(Cl);
based on the total weight of the pre-formulation.

In a further preferred embodiment of the invention the pre-formulation comprises:
a) 33-43 wt % GDO;
b) 33-55 wt % SPC;
c) 8-18 wt % EtOH and PG;
d) 0.001-0.020 wt % EDTA;
e) 0.1-12 wt % OCT(Cl);
based on the total weight of the pre-formulation.

In a further preferred embodiment of the invention the pre-formulation comprises:
a) 42.3 wt % GDO;
b) 42.3 wt % SPC;
c) 6.5 wt % EtOH and 6.5 wt % PG;
d) 0.010 wt % EDTA and 0.008 wt % ETA;
e) 2.27 wt % OCT(Cl);
based on the total weight of the pre-formulation;
and wherein the wt % values may vary with +/−20%, preferably +/−10%, more preferably +/−5% of said wt % values.

The term "pre-formulation" herein is a pharmaceutical composition, preferably is a parenteral pharmaceutical composition, more preferably is an injectable parenteral pharmaceutical composition, even more preferably is an injectable parenteral pharmaceutical composition for subcutaneous or intra-muscular application, even more preferably is an injectable parenteral pharmaceutical composition for subcutaneous application.

Optional Additional Components

In one particularly preferred embodiment of the present invention, the compositions (pre-formulations and resulting depots) do not include fragmentation agents, such as polyethyleneoxide or poly(ethylene glycol) (PEG) fragmentation agent, e.g. a PEG grafted lipid and/or surfactant.

For example, the compositions preferably do not include fragmentation agents such as Polysorbate 80 (P80), or other Polysorbates (e.g. Polysorbate 20), PEGylated phospholipids (PEG-lipids such as DSPE-PEG(2000), DSPE-PEG (5000), DOPE-PEG(2000) and DOPE-PEG(5000)), Solutol HS 15, PEGylated fatty acids (e.g. PEG-oleate), block co-polymers such as Pluronic® F127 and Pluronic® F68, ethoxylated castor oil derivatives (e.g. Chremophores), PEGylated glyceryl fatty acid esters (such as TMGO-15 from Nikko Chemicals) and PEGylated tocopherols (such as d-alpha tocopheryl poly(ethylene glycol)1000 succinate known as Vitamin E TPGS from Eastman.

However, the active agent as a powder (e.g. in the kit of the invention), as well as active agent dissolved in the lipid formulation, may gain stability (both storage and in vivo stability) by certain stabilising additives. Such additives include sugars (e.g. sucrose, trehalose, lactose etc.), polymers (e.g. polyols such as carboxy methyl cellulose), amino acids (such as methionine, glutamate, lysine etc.), lipid-soluble acid components such as HC1, anionic lipids and/or surface active agents (such as dioleoyl phosphatidyl glycerol (DOPG), palmitoyloleoyl phosphatidylglycerol (POPG) and oleic acid (OA)).

Single-dose formats must remain stable and potent in storage prior to use, but are disposable after the single use. It is a remarkable finding that non-aqueous pre-formulations comprising an alkylammonium EDTA salt have enhanced storage stability at elevated temperatures, such as at 25° C. or even 40° C. This offers advantages in terms of ease of transportation and storage (no need for refrigeration). It is preferred that a single dose format has a stability such that after storage for 2 months at 25° C. (with air in head space), the assayed active agent concentration is at least 95% that of the initial assayed active agent concentration, and after 3 months, the assayed active agent concentration is at least 90% that of the initial assayed active agent concentration.

It is preferred that a single dose format has a stability such that after storage for 2 months at 40° C. (with air in head space), the assayed active agent concentration is at least 85% that of the initial assayed active agent concentration, and after 3 months, the assayed active agent concentration is at least 80% that of the initial assayed active agent concentration.

Multi-dose formats must not only remain stable and potent in storage prior to use, but must also remain stable, potent and relatively/effectively free of bacteria over the multiple-dose use regimen administration period after the first use in which a seal has been compromised. For this reason multi-dose formats often require an antimicrobial or microbial-static agent, e.g. bacteriostatic agent, preservative.

However, the production of preserved pharmaceutical preparations containing protein or peptide actives has often proven difficult, as when preservatives are used, these give rise to stability problems. Often the proteins are inactivated and aggregates are formed, which may sometimes lead to reported injection site intolerance or immunogenicity to the active. This can be further aggravated by additional excipients or formulation components.

In one aspect each of the embodiments herein can optionally contain an antimicrobial or microbial-static agent, which includes bacteriostatic agents and preservative. Such agents include benzalkonium chloride, m-cresol, benzyl alcohol or other phenolic preservatives. Typical concentrations as known in the art can be used.

Additional components above those mentioned as components a) to e) will, where present at all, preferably be present in an amount of 0 to 5% (e.g. 0.01% to 5%) by weight, preferably no more than 2% by weight and more preferably no more than 1% by weight.

In one embodiment, components a) and b) (allowing for any impurity inherent in the nature of these components) make up at least 95% of the lipid components of the composition. Preferably at least 99% of the total lipid content of the pre-formulation consists of components a) and b). Preferably the lipid component of the pre-formulation consists essentially of components a) and b).

Administration

The pre-formulations of the present invention are generally formulated to be administered parenterally. This administration will generally not be an intra-vascular method but will preferably be subcutaneous (s.c.), intracavitary or intramuscular (i.m.). Typically the administration will be by injection, which term is used herein to indicate any method in which the formulation is passed through the skin, such as by needle, catheter or needle-less (needle-free) injector. Preferred parenteral administration is by i.m or s.c. injection, most preferably by deep s.c. injection. An important feature of the composition of the invention is that it can be administered both by i.m. and s.c. and other routes without toxicity or significant local effects. It is also suitable for intracavital administration. The deep s.c. injection has the advantage of being less deep and less painful to the subject than the (deep) i.m. injection used for some current depots and is technically most suitable in the present case as it combines ease of injection with low risk of local side effects. It is a surprising observation of the present inventors that the formulations provide sustained release of active agent over a predictable time period by both subcutaneous and intramuscular injection. This therefore allows the site of injection to be varied widely and allows the dose to be administered without detailed consideration of the tissue depth at the site of injection.

In one embodiment the lipid pre-formulations of the present invention provide non-lamellar liquid crystalline depot compositions upon exposure to aqueous fluids, especially in vivo. As used herein, the term "non-lamellar" is used to indicate a normal or reversed liquid crystalline phase (such as a cubic or hexagonal phase) or the L3 phase or any combination thereof. The term liquid crystalline indicates all hexagonal, all cubic liquid crystalline phases and/or all mixtures thereof. Hexagonal as used herein indicates "normal" or "reversed" hexagonal (preferably reversed) and "cubic" indicates any cubic liquid crystalline phase unless specified otherwise. The skilled reader will have no difficulty in identifying those compositions having appropriate phase behaviour by reference to the description and Examples provided herein, and to WO2005/117830, but the most favoured compositional area for phase behaviour is where ratio of components a:b are in the region of 40:60 to 70:30, preferably 45:55 to 55:45 and more preferably 40:60 to 54:46. Ratios of around 50:50 (e.g. 49:51 to 51:49) are highly preferred, most preferably around 50:50.

It is important to appreciate that the pre-formulations of the present invention are of low viscosity. As a result, these pre-formulations must not be in any bulk liquid crystalline phase since all liquid crystalline phases have a viscosity significantly higher than could be administered by syringe or similar injecting dispenser. The pre-formulations of the present invention will thus be in a non-liquid crystalline state, such as a solution, $L_2$ or $L_3$ phase, particularly solution or $L_2$. The $L_2$ phase as used herein throughout is preferably a "swollen" $L_2$ phase containing greater than 5 wt %, preferably greater than 7%, and most preferably greater than 9% of organic mono-alcoholic solvent (component c) having a viscosity reducing effect.

The pre-formulations described herein are preferably of "low viscosity". This may be indicated, for example by the ability to be dispensed from a 1 ml disposable syringe through a small gauge needle. Preferably, the low viscosity mixtures can be dispensed through a needle of 19 awg, preferably smaller than 19 gauge, more preferably 23 awg (or most preferably even 27 gauge) needle by manual pressure. In a particularly preferred embodiment, the low viscosity mixture should be a mixture capable of passing through a standard sterile filtration membrane such as a 0.22 µm syringe filter. A typical range of suitable viscosities for the pre-formulations of the invention would be, for example, 1 to 1000 mPas, preferably 10 to 800 mPas, more preferably 50 to 750 mPas and most preferably 50 to 600 mPas at 20° C.

Upon administration, many of the preferred lipid-based pre-formulations of the present invention undergo a phase structure transition from a low viscosity mixture to a high viscosity (generally tissue adherent) depot composition. Generally this will be a transition from a molecular mixture, swollen $L_2$ and/or $L_3$ phase to one or more (high viscosity) liquid crystalline phases such as normal or reversed hexagonal or cubic liquid crystalline phases or mixtures thereof. Further phase transitions may also take place following administration. Obviously, complete phase transition is not necessary for the functioning of the invention but at least a surface layer of the administered mixture will form a liquid crystalline structure. Generally this transition will be rapid for at least the surface region of the administered formulation (that part in direct contact with air, body surfaces and/or body fluids). This will most preferably be over a few seconds or minutes (e.g. from 1 second up to 30 minutes, preferably up to 10 minutes, more preferably 5 minutes of less). The remainder of the composition may change phase to a liquid crystalline phase more slowly by diffusion and/or as the surface region disperses.

Without being bound by theory, it is believed that upon exposure to excess aqueous fluid, the pre-formulations of the invention lose some or all of the organic solvent included therein (e.g. by diffusion) and take in aqueous fluid from the bodily environment (e.g. the in vivo environment). For certain lipid pre-formulations as described herein, at least a part of the formulation preferably generates a non-lamellar, particularly liquid crystalline phase structure. In most cases these non-lamellar structures are highly viscous and are not easily dissolved or dispersed into the in vivo environment. The result is a monolithic "depot" generated in vivo with only a limited area of exposure to body fluids. Furthermore, because the non-lamellar structure has large polar, apolar and boundary regions, the lipid depot is highly effective in solubilising and stabilising active agents such as peptides and protecting these from degradation mechanisms. As the depot composition formed from the pre-formulation gradually degrades over a period of days, weeks or months, the active agent is gradually released and/or diffuses out from the composition. Since the environment within the depot composition is relatively protected, the pre-formulations of the invention are highly suitable for active agents with a relatively low biological half-life (see above).

By incorporation of a co-solvent into the pre-formulations, as described for the first time in WO2012/160213, it is believed that the rate of phase transition to a non-lamellar (e.g. liquid crystalline) phase at the surface of the injected pre-formulation can be enhanced in comparison with compositions containing organic solvents in the substantial absence of water. The performance of the resulting depot is thus improved and further control over the release of active agent achieved.

The depot systems formed by the formulations of the present invention are highly effective in protecting the active agent from degradation and thus allow an extended release period. The formulations of the invention thus may provide in vivo depots of peptide active agents which require administration only once every 5 to 90 days preferably 5 to 60 days, more preferably 6 to 32. Evidently, a longer stable release period is desirable for patient comfort and compliance, as well as demanding less time from health professionals if the composition is not to be self-administered. Where the composition is to be self-administered, patient compliance may be aided by a weekly (e.g. every 7 days, optionally±1 day), bi-seekly (e.g. every 14 days, optionally±2 days) or monthly (e.g. every 28 or 30 days (optionally±7 days) administration so that the need to administer is not forgotten.

A considerable advantage of the depot precursors of the present invention is that they are stable homogeneous phases. That is to say, they may be stored for considerable periods (preferably at least 6 months) at room or refrigerator temperature, without phase separation. As well as providing advantageous storage and facile administration, this allows for the dose of somatostatin receptor agonist to be selected by reference to the species, age, sex, weight, and/or physical condition of the individual subject, by means of injecting a selected volume.

The present invention thus provides for methods comprising the selection of a dosing amount specific to an individual, particularly by subject weight. The means for this dose selection is the choice of administration volume.

In one preferred aspect, the present invention provides a pre-formulation comprising components a), b), c), d), and e), and 0-1.0% water. The amounts of these components will typically be in the range 20-60% a), 20-60% b), 1-30% c) and 0.001-0.8% d).

The pre-formulations of the present invention are highly advantageous in that they are stable to prolonged storage in their final "administration ready" form. As a result, they may readily be supplied for administration either by health professionals or by patients or their carers, who need not be fully trained health professionals and may not have the experience or skills to make up complex preparations. This is particularly important in long-duration, slow-effecting diseases such as diabetes.

Devices

In a yet further aspect, the present invention provides a disposable administration device (which is also to include a device component) pre-loaded with a measured dose of a pre-formulation of the present invention. Such a device will typically contain a single dose ready for administration, and will generally be sterile-packed such that the composition is stored within the device until administration. Suitable devices include cartridges, ampoules and particularly syringes and syringe barrels, either with integral needles or with standard (e.g. luer) fittings adapted to take a suitable disposable needle.

For a device comprising a single dose of a pre-formulation comprising octreotide, an amount of octreotide of 10 to 180 mg would be suitable for providing a therapeutic level for between 7 and 90 days.

Preferably, the amount of octreotide will be around 0.2 to 3 mg per day between injections. Thus a depot administered every 30 days would have 6 to 90 mg or a 90 day depot have 18 to 270 mg of octreotide.

For Pasireotide, the dosage would typically be an amount of around 0.05 to 40 mg per week of depot duration, preferably 0.1 to 20 mg per week duration (e.g. 1 to 5 mg per week) for a duration of 1 to 24 weeks, preferably 2 to 16 (e.g. 3, 4, 8, 10 or 12) weeks. In an alternative embodiment the pre-formulation may be formulated for dosing weekly (e.g. every 7±1 days). A total dose of 0.05 to 250 mg of Pasireotide per dose would be suitable for providing a therapeutic level for between 7 and 168 days. This will preferably be 0.1 to 200 mg, e.g. 0.2 to 150 mg, 0.1 to 100 mg, 20 to 160 mg etc. Evidently, the stability of the active and effects on the release rate will mean that the loading to duration may not be a linear relationship. A depot administered every 30 days might have, for example 0.2 to 20 mg of Pasireotide, or a 90 day depot might have 30 to 60 mg of Pasireotide.

Kits

The pre-filled devices of the invention may also suitably be included in an administration kit, which kit also forms a further aspect of the invention. In a still further aspect, the invention thus provides a kit for the administration of at least one somatostatin receptor agonist, said kit containing a measured dose of a formulation of the invention and optionally an administration device or component thereof. Preferably the dose will be held within the device or component, which will be suitable for i.m. or preferably s.c. administration. The kits may include additional administration components such as needles, swabs, etc. and will optionally and preferably contain instructions for administration. Such instructions will typically relate to administration by a route as described herein and/or for the treatment of a disease indicated herein above.

The invention provides for a pre-filled administration device as indicated herein and a kit as indicated herein comprising a pre-formulation as described herein.

In an alternative aspect of the present invention, the "kit" may contain at least two vessels, a first containing a low viscosity mixture of components a) to d), as described here, and a second containing a measured dose of at least one active agent as described herein.

Such a "two component kit" may comprise the active agent as a powder formulation in one vial or pre-filled syringe and components a) to d) in a second vial or pre-filled syringe. In the case of two syringes, before injection, the pre-filled syringes are connected and the powder comprising active agent is mixed with the matrix formulation by moving the syringe barrels back and forth, forming a solution or suspension which is injected. Alternatively, the liquid lipid formulation is drawn from one vial, or is pre-filled into a syringe, and is injected into a vial containing powdered active agent (e.g. peptide). This formulation may subsequently be mixed by hand shaking or other suitable reconstitution method (e.g. vortex mixing etc.).

The solvent component may be present in either or both vessels (e.g. vials or syringes). Where the solvent is at least partially constituted with the active agent, this will generally be in the form of a solution or suspension.

In this aspect, the invention therefore provides a two component kit comprising
i) a first vessel containing a low viscosity mixture of components a) to c) as described herein;
ii) an optional second vessel containing at least one peptide active agent,
iii) an antioxidant component d) optionally in a third vessel, preferably in the second vessel, or most preferably in the first vessel;
iv) optionally and preferably at least one of:
  1) at least one syringe (which may be one or both of said first and second vessels);

2) a needle for administration, such as those described herein;
3) instructions for generation of a composition of the invention from the contents of the first and second vessels;
4) instructions for administration, whereby to form a depot as described herein.

Preferred Features and Combinations

In combination with the features and preferred features indicated herein, the pre-formulations of the invention may have one or more of the following preferred features independently or in combination:

All proportions indicated herein may optionally be varied by up to 10% of the amount specified, optionally and preferably by up to 5%;

Component a) comprises, consists essentially of or preferably consists of GDO;

Component b) comprises, consists essentially of or preferably consists of soy PC;

Component c) comprises, consists essentially of or preferably consists of a 1, 2, 3 or 4 carbon alcohol, preferably isopropanol or more preferably ethanol;

Component c) includes a polar co-solvent such as propylene glycol;

The pre-formulation contains octreotide;

The pre-formulation contains at least one somatostatin receptor agonist (as described herein) which has agonistic and/or antagonistic effect at at least one of the SST(1)-SST(5) receptors (e.g. in humans);

The pre-formulation has a low viscosity as indicated herein;

The pre-formulation forms a non-lamellar liquid crystalline phase as indicated herein upon in vivo administration;

The pre-formulation generates a depot following in vivo administration, which depot releases at least one active agent at a therapeutic level over a period of at least 7 days, preferably at least 21 days, more preferably at least 28 days;

In combination with the features and preferred features indicated herein, the method(s) of treatment of the present invention may have one or more of the following preferred features independently or in combination:

The method comprises the administration of at least one formulation with one or more preferred features as indicated above;

The method comprises the administration of at least one formulation as indicated herein by i.m., s.c. (e.g. deep s.c.) injection;

The method comprises administration by means of a pre-filled administration device as indicated herein;

The method comprises administration through a needle no larger than 20 gauge, preferably smaller than 20 gauge, and most preferably 22 gauge, 23 gauge or smaller;

The method comprises a single administration every 5 to 90 days, preferably 6 to 32 days (for example 7 days or 28-31 days).

In combination with the features and preferred features indicated herein, the use(s) of the pre-formulations indicated herein in the manufacture of medicaments may have one or more of the following preferred features independently or in combination:

The use comprises the use of at least one formulation with one or more preferred features as indicated above;

The use comprises the manufacture of a medicament for administration of at least one formulation as indicated herein by i.m. or s.c. injection;

The use comprises the manufacture of a medicament for administration by means of a pre-filled administration device as indicated herein;

The use comprises the manufacture of a medicament for administration through a needle no larger than 20 gauge, preferably smaller than 20 gauge, and most preferably 22 gauge, 23 gauge or smaller;

The use comprises the manufacture of a medicament for administration once every 5 to 90 days, preferably 5 to 60 days, more preferably 6 to 32 days.

In combination with the features and preferred features indicated herein, the pre-filled devices of the invention may have one or more of the following preferred features independently or in combination:

They contain a preferred formulation as indicated herein;

They comprise a needle smaller than 20 gauge, preferably no larger than 22 gauge or no larger than 23 gauge;

They contain a peptide active agent Somatostatin receptor agonist (e.g. octreotide) at around 1 to 100 mg.

They contain a homogeneous mixture of a composition of the invention in ready-to-inject form.

They contain a formulation of components a) to d) for combination with an active agent.

They contain a total volume for administration of no more than 5 ml, preferably no more than 3 ml more preferably no more than 1.5 ml.

In combination with the features and preferred features indicated herein, the kits of the invention may have one or more of the following preferred features independently or in combination:

They contain a preferred formulation as indicated herein;

They contain a pre-filled device as indicated herein;

They contain a needle smaller than 20 gauge, preferably no larger than 22 gauge or no larger than 23 gauge;

They contain a single dose of 1 to 200 mg of peptide somatostatin receptor agonist, preferably 1 to 100 mg and more preferably 1-50 mg;

They contain octreotide, at around 1 to 100 mg;

They contain a total volume for administration of no more than 5 ml, preferably no more than 3 ml more preferably no more than 1.5 ml.

They contain instructions for administration by a route and/or at a frequency as indicated herein;

They contain instructions for administration for use in a method of treatment as described herein.

The Invention will now be further illustrated by reference to the following non-limiting Examples and the attached Figures.

EXAMPLES

Materials

All materials used in the Examples were obtained from commercial sources and were of pharmacopoeial grade where applicable or of the highest purity grade available. The following abbreviations are used throughout the Examples:
API Active pharmaceutical ingredient
DiETA Diethanolamine
DTPA Diethylenetriaminepentaacetic (pentetic) acid
EtOH Ethanol (99.7% Ph. Eur)
EDTA Ethylenediaminetetraacetic (edetic) acid (USP/NF)
EDTA(Na) Ethylenediaminetetraacetic acid disodium dihydrate
ETA Ethanolamine (USP/NF)
$FeCl_3 \times 6H_2O$ Iron(III) chloride hexahydrate GDO Glycerol dioleate (Cithrol GDO HP-SO-(LK) from Croda)
OCT(Cl) Octreotide hydrochloride
PG Propylene glycol (Ph. Eur)
SOM(Ac) Somatostatin-14 acetate
SOM(Cl) Somatostatin-14 chloride
SPC Soy phosphatidylcholine (Lipoid S100 from Lipoid)
TRIS Tris(hydroxymethyl)aminomethane General Procedures Preparation of EDTA and EDTA(Na) Solutions in EtOH/PG Samples were prepared by weighing the appropriate amounts of EDTA or EDTA(Na) and alkylamine into glass vials, e.g. 15R vials, followed by addition of organic solvent or solvent mixture (e.g EtOH/PG (50/50 w/w)). Vials were sealed and placed on either a roller mixer by end-over-end rotation at ambient RT or magnetic stirrer. During dissolution, vials were visually inspected for undissolved EDTA particles using ambient and cross-polarized light.

Preparation of $FeCl_3 \times 6H_2O$ Solutions

Samples were prepared by weighing the appropriate amount of $FeCl_3 \times 6H_2O$ into sterilized glass vials followed by addition of organic solvent or solvent mixture. Vials were sealed and placed on a roller mixer by end-over-end rotation at ambient RT until $FeCl_3 \times 6H_2O$ was completely dissolved.

Preparation of SOM(Cl)

For the ion-exchange process, approximately 120 g of Dowex 1×2 chloride form (50-100 mesh) resin was mixed with an equal amount of Millipore water, added to a 200 mL glass ion-exchange column and left to equilibrate overnight. Next day, prior to ion-exchange the Dowex matrix was slowly washed with 900 ml Millipore water and the ion-exchange process was initiated. 3.743 g of SOM(Ac) was dissolved in 112.4 g Millipore water. Freshly prepared (within approx. 30 min) SOM(Ac) solution was loaded onto the top of the ion-exchange column. The flow (at approx. 15 s/mL) was initiated and eluate fractions of 50-250 mL each were collected by continuously rinsing the column with Millipore water. The eluate fractions with conductivity greater than 50 μS/cm were pooled, transferred into three 1000 mL round-bottom flasks, shell-frozen in EtOH/dry-ice using Rotavapor R-200, placed to cool at −80° C. for about 1 h and lyophilized overnight for about 36 h. The obtained amount and yield of SOM(Cl) were 3.096 g and 82.7%, respectively. The complete exchange of acetate to chloride was confirmed by determination of the two anions by indirect HPLC-UV.

Preparation of Lipid Formulations

Lipid placebo formulations were prepared by weighing appropriate amounts of SPC, GDO, EDTA/alkylamine solution, and $FeCl_3 \times 6H_2O$ (when needed) solution into sterilized glass vials. The sealed vials were then placed on a roller mixer at room temperature until mixed completely into clear homogeneous liquid solution (<24 hours).
API-containing formulations were prepared by adding appropriate amounts of API powder to the lipid placebo formulations in sterilized glass vials. The vials were sealed and placed on a roller mixer at room temperature until mixed completely into clear homogeneous liquid solution (ca. 24 hours).

As an example, EDTA and ETA (at EDTA:ETA molar ratio 1:4) were dissolved in EtOH/PG (50/50 w/w) mixture. Then, appropriate amounts of SPC, GDO (at SPC/GDO weight ratio 50/50) and EtOH/PG/EDTA/ETA mixture were weighed into a sterilized 20R glass vial. The sealed vial was then placed on a roller mixer at room temperature until mixed completely into clear homogeneous liquid solution (<24 hours). OCT(Cl) powder was then added to the lipid formulations in sterilized 15R glass vial at 2.34 wt % concentration. The vial was sealed and placed on a roller mixer at room temperature until mixed completely into clear homogeneous liquid solution (24 hours).

Evaluation of Octreotide Stability in Lipid Formulations (Typical Method)

Prepared lipid peptide (e.g. octreotide) formulations as above were divided into sterilized 2R glass vials (0.5 g of formulation per vial). The head space of the vials was ambient air, i.e., no inert atmosphere such as nitrogen was introduced in the head space. Vials were sealed and placed in controlled environment storage cabinets at 25° C./60% RH and 40° C./75% RH. At predefined sampling points (up to three months of storage) two vials of each formulation and storage cabinet were withdrawn, equilibrated to room temperature for 1 hour and analyzed for peptide content (assay) using gradient HPLC with UV detection.

It should be noted that the filling procedure and storage conditions ensured forced degradation conditions as the head space was composed of air rather than inert atmosphere such as nitrogen.

HPLC-UV Determination of Peptides in Lipid Formulations

Determination of peptide (e.g. octreotide, such as octreotide chloride) in lipid formulations was carried out by gradient HPLC with UV detection. The HILIC analytical column used was a HALO Penta-HILIC 2.7 μm, 150×3.0 mm. Quantification was carried out by interpolating the peptide (e.g. octreotide) peak area obtained in lipid formulation samples (prepared by dissolving the lipid formulation in a sample solvent at the required target peptide concentration) into the calibration curves generated from standard solutions containing known concentrations of the corresponding peptide.

A typical mobile phases used (for example with octreotide) consisted of water:2M sodium chloride:acetonitrile:trifluoroacetic acid 384:16:400:1 (v/v) (mobile phase A) and water:methanol:acetonitrile:trifluoroacetic acid 20:30:950:1 (v/v) (mobile phase B). The detection was carried out at 220 nm. The sample solvent used was acetonitrile:methanol (1:1, v/v); octreotide eluted after approximately 25.2 min.

Data Presentation

In the example section, in addition to absolute API assay values, results are also in some cases expressed as a Stability Index for API assay. The Stability Index is calculated as the API assay value in the particular formulation divided by the API assay value in the reference formulation. Expressed in this way, Stability Index values greater than 1 means improved API stability when compared to the reference formulation.

Measurement of Vial Headspace Oxygen Concentration

Oxygen concentration in the vial headspace was measured using a PC-controlled PreSens Microx TX3 micro fiber optic oxygen transmitter equipped with a needle-type optical oxygen microsensor (NTH, 140 µm flat broken tip). Measurements were performed by penetrating the oxygen microsensor through the vial rubber stopper into the vial headspace and measuring the oxygen concentration until a stable readout was obtained (about 1 min).

Example 1. EDTA Solubility in the Presence and Absence of Alkylamine 0.08 wt % EDTA and EDTA(Na) solutions in EtOH/PG (50/50 w/w) were prepared in the presence and absence of ETA (Table 1). Dissolution of EDTA and EDTA(Na) during end-over-end rotation at ambient RT was assessed by visual inspection (ambient and crossed-polarized light) over 27 days. The results show that neither the disodium salt (EDTA (Na)) nor the acid form of EDTA is soluble in EtOH/PG without using ETA even after 27 days of mixing. The obtained results also show that EDTA(Na) is not soluble in EtOH/PG even in the presence of ETA whereas the acid form of EDTA is solubilized in EtOH/PG in the presence of 4 mol ETA per 1 mol of EDTA already after 24 hours mixing.

TABLE 1

Solubility of 0.08 wt % EDTA and EDTA(Na) in EtOH/PG in the presence and absence of ETA.

| Sample No | EDTA type | ETA/EDTA (mol/mol) | Observations after mixing for 24 h | 27 days |
|---|---|---|---|---|
| Sample 1 | Disodium dihydrate | 0.00 | Not soluble | Not soluble |
| Sample 2 | Acid form | 0.00 | Not soluble | Not soluble |
| Sample 3 | Disodium dihydrate | 3.94 | Not soluble | Not soluble |
| Sample 4 | Acid form | 3.95 | Soluble | Soluble |

Example 2. EDTA Solubility as a Function of ETA/EDTA Molar Ratio

Table 2 summarizes results on EDTA solubility at a concentration of 0.38 wt % in EtOH/PG solvent mixtures (1/1 wt/wt) as a function of ETA/EDTA molar ratio. The only sample where EDTA was not fully dissolved was for the lowest ETA/EDTA molar ratio. In all other samples EDTA was soluble after 24 h end-over-end rotation mixing at ambient RT. The obtained results show that about 3.5 mol of ETA per 1 mol of EDTA is close to the required minimum amount needed to solubilize EDTA in the non-aqueous solvent used.

TABLE 2

Solubility of 0.38 wt % EDTA in EtOH/PG as a function of ETA/EDTA molar ratio.

| Sample ID | ETA/EDTA (mol/mol) | EDTA solubility (ca 24 h mixing) |
|---|---|---|
| Sample 5 | 2.83 | Not soluble |
| Sample 6 | 3.49 | Soluble |
| Sample 7 | 3.90 | Soluble |
| Sample 8 | 3.90 | Soluble |
| Sample 9 | 4.02 | Soluble |
| Sample 10 | 3.99 | Soluble |
| Sample 11 | 4.30 | Soluble |
| Sample 12 | 4.24 | Soluble |
| Sample 13 | 4.45 | Soluble |
| Sample 14 | 4.48 | Soluble |
| Sample 15 | 4.62 | Soluble |
| Sample 16 | 4.65 | Soluble |

Example 3. EDTA Solubility as a Function of DiETA/EDTA Molar Ratio

Table 3 summarizes EDTA solubility results in EtOH/PG (1/1 wt/wt) solvent mixture at 0.38 wt % EDTA as a function of DiETA/EDTA molar ratio after 24 h end-over-end rotation mixing at ambient RT. The obtained results show that about 4.5 mol of DiETA per 1 mol of EDTA is close to the required minimum amount needed to solubilize EDTA in non-aqueous solvent used.

TABLE 3

Solubility of 0.38 wt % EDTA in EtOH/PG as a function of DiETA/EDTA molar ratio.

| Sample ID | DiETA/EDTA (mol/mol) | EDTA solubility (ca 24 h mixing) |
|---|---|---|
| Sample 17 | 2.14 | Not soluble |
| Sample 18 | 2.68 | Not soluble |
| Sample 19 | 3.20 | Not soluble |
| Sample 20 | 3.52 | Almost fully soluble |
| Sample 21 | 3.97 | Soluble or almost fully soluble |
| Sample 22 | 4.51 | Soluble |
| Sample 23 | 5.09 | Soluble |

Example 4. EDTA Solubility as a Function of Ethylenediamine/EDTA Molar Ratio

Table 4 summarizes EDTA solubility results in EtOH/PG (1/1 wt/wt) solvent mixture at 0.38 wt % EDTA as a function of ethylenediamine/EDTA molar ratio after 24 h end-over-end rotation mixing at ambient RT. The obtained results showed that about 2.5 mol of ethylenediamine per 1 mol of EDTA is close to the required minimum amount needed to solubilize EDTA in non-aqueous solvent used.

TABLE 4

Solubility of 0.38 wt % EDTA in EtOH/PG as a function of ethylenediamine/EDTA molar ratio.

| Sample ID | Ethylenediamine/EDTA (mol/mol) | EDTA solubility (ca 24 h mixing) |
|---|---|---|
| Sample 24 | 1.96 | Not soluble |
| Sample 25 | 2.45 | Soluble |
| Sample 26 | 3.09 | Soluble |
| Sample 27 | 3.46 | Soluble |

TABLE 4-continued

Solubility of 0.38 wt % EDTA in EtOH/PG as a
function of ethylenediamine/EDTA molar ratio.

| Sample ID | Ethylenediamine/EDTA (mol/mol) | EDTA solubility (ca 24 h mixing) |
|---|---|---|
| Sample 28 | 3.92 | Soluble |
| Sample 29 | 4.47 | Soluble |
| Sample 30 | 5.00 | Soluble |

Example 5. EDTA Solubility as a Function of Serinol/EDTA Molar Ratio

Table 5 summarizes EDTA solubility results in EtOH/PG (1/1 wt/wt) solvent mixture at 0.38 wt % EDTA as a function of serinol/EDTA molar ratio after 24 h end-over-end rotation mixing at ambient RT. The obtained results showed that about 4 mol of serinol per 1 mol of EDTA is close to the required minimum amount needed to solubilize EDTA in non-aqueous solvent used.

TABLE 5

Solubility of 0.38 wt % EDTA in EtOH/PG as
a function of serinol/EDTA molar ratio.

| Sample ID | Serinol/EDTA (mol/mol) | EDTA solubility (ca 24 h mixing) |
|---|---|---|
| Sample 31 | 1.88 | Not soluble |
| Sample 32 | 2.36 | Not soluble |
| Sample 33 | 3.32 | Not soluble |
| Sample 34 | 3.48 | Almost soluble |
| Sample 35 | 4.11 | Soluble |
| Sample 36 | 4.77 | Soluble |
| Sample 37 | 5.09 | Soluble |
| Sample 38 | 5.45 | Soluble |

Example 6. EDTA Solubility as a Function of TRIS/EDTA Molar Ratio

Table 6 summarizes EDTA solubility results in EtOH/PG (1/1 wt/wt) solvent mixture at 0.38 wt % EDTA as a function of TRIS/EDTA molar ratio after 7 days end-over-end rotation mixing at ambient RT. The obtained results showed that about 5 mol of TRIS per 1 mol of EDTA is close to the required minimum amount needed to solubilize EDTA in non-aqueous solvent used.

TABLE 6

Solubility of 0.38 wt % EDTA in EtOH/PG
as a function of TRIS/EDTA molar ratio.

| Sample ID | TRIS/EDTA (mol/mol) | EDTA solubility (ca 7 days mixing) |
|---|---|---|
| Sample 39 | 2.03 | Not soluble |
| Sample 40 | 2.57 | Not soluble |
| Sample 41 | 2.96 | Not soluble |
| Sample 42 | 3.52 | Not soluble |
| Sample 43 | 3.97 | Almost soluble |
| Sample 44 | 4.49 | Almost soluble |
| Sample 45 | 5.04 | Soluble |
| Sample 46 | 4.98 | Soluble |
| Sample 47 | 5.55 | Soluble |
| Sample 48 | 5.98 | Soluble |
| Sample 49 | 6.48 | Soluble |
| Sample 50 | 6.97 | Soluble |
| Sample 51 | 7.47 | Soluble |
| Sample 52 | 8.03 | Soluble |

Example 7. Stability of OCT(Cl) in Lipid Formulations in the Presence of EDTA Lipid formulations containing 2.34 wt % of OCT(Cl) in the presence and absence of 100 ppm of EDTA were prepared according to the compositions given in Table 7. Formulations were divided into sterilized 2R glass vials (0.5 g of formulation per vial), sealed and placed in controlled environment storage cabinets at either 40° C./75% RH or 25° C./60% RH. The headspace of the vials was ambient air to ensure forced degradation conditions, i.e., no inert atmosphere such as nitrogen was introduced. At predefined sampling points (up to three months of storage), two vials of each formulation and storage condition were withdrawn from the controlled environment cabinets, equilibrated to room temperature for 1 hour and analyzed for peptide content (assay) using gradient HPLC with UV detection.

TABLE 7

OCT(Cl) containing FluidCrystal ® formulation
compositions (in wt %) with and without EDTA.

| Sample ID | OCT(Cl) | SPC | GDO | EtOH | PG | ETA | EDTA |
|---|---|---|---|---|---|---|---|
| Sample 53 | 2.34 | 42.33 | 42.33 | 6.50 | 6.50 | — | — |
| Sample 54 | 2.34 | 42.32 | 42.32 | 6.50 | 6.50 | 0.01 | 0.01 |

Samples of the two formulations were placed on stability as described under General Procedures. It should be noted that the filling procedure and storage conditions ensured forced degradation conditions as the head space was composed of air rather than inert atmosphere such as nitrogen. FIG. 1 presents the octreotide assay at different storage time points and storage conditions. As shown in FIG. 1, the presence of 0.01 wt % (100 ppm) of EDTA solubilized in the lipid formulation by the use of 0.01 wt % (100 ppm) ETA dramatically enhanced the peptide stability at both storage conditions.

Example 8. Effect of EDTA Concentration on Peptide Stability

Lipid formulations containing 2.27 wt % of OCT(Cl) and different concentrations of EDTA were prepared according to the compositions given in Table 8. Formulations were divided into sterilized 2R glass vials (0.5 g of formulation per vial), sealed and placed in controlled environment storage cabinets at either 40° C./75% RH or 25° C./60% RH. The head space of the vials was ambient air to ensure forced degradation conditions, i.e., no inert atmosphere such as nitrogen was introduced. At predefined sampling points (up to six months of storage) two vials of each formulation and storage condition were withdrawn from the controlled environment cabinets, equilibrated to room temperature for 1 hour and analyzed for peptide content (assay) using gradient HPLC with UV detection.

TABLE 8

Formulation compositions with different concentrations of EDTA (all components in wt %) comprising 2.27 wt % OCT(Cl).

| Sample ID | OCT(Cl) | SPC | GDO | EtOH | PG | ETA | EDTA |
|---|---|---|---|---|---|---|---|
| Sample 55 | 2.27 | 42.37 | 42.37 | 6.50 | 6.50 | — | — |
| Sample 56 | 2.27 | 42.36 | 42.36 | 6.50 | 6.50 | 0.004 | 0.005 |
| Sample 57 | 2.27 | 42.36 | 42.36 | 6.50 | 6.50 | 0.008 | 0.010 |
| Sample 58 | 2.27 | 42.34 | 42.34 | 6.50 | 6.50 | 0.021 | 0.025 |
| Sample 59 | 2.27 | 42.32 | 42.32 | 6.50 | 6.50 | 0.042 | 0.050 |
| Sample 60 | 2.27 | 42.30 | 42.30 | 6.50 | 6.50 | 0.063 | 0.075 |

Samples of the six formulations were placed on stability as described under General Procedures. It should be noted that the filling procedure and storage conditions ensured forced degradation conditions as the head space was composed of air rather than inert atmosphere such as nitrogen. The results are shown in FIG. 2. As shown, the presence of EDTA solubilized in the lipid formulation with the help of ETA dramatically enhanced the peptide stability vs. the reference formulation not containing EDTA/ETA. The maximum stabilization effect was achieved within the concentration interval 50-250 ppm (0.005-0.025 wt %) EDTA.

Example 9. Long-term Stability of OCT(Cl) in Lipid Formulations in the Presence of EDTA Lipid formulations containing OCT(Cl) in the absence and presence of 100 ppm EDTA were prepared according to the compositions given in Table 9. Formulations were divided into sterilized 1 mL 22G×½" glass syringes (Schott AG) (0.5 g of formulation per syringe), sealed with plunger and placed in a controlled environment storage cabinet at 25° C./60% RH. At predefined sampling points (up to twelve months of storage), two syringes of each formulation were withdrawn from the controlled environment cabinet, equilibrated to room temperature for 1 hour and analyzed for peptide content (assay) using gradient HPLC with UV detection.

TABLE 9

OCT(Cl) containing lipid formulation compositions (in wt %) without and with EDTA. The octreotide content corresponds to 20 mg/mL octreotide free base when corrected for peptide content, purity and formulation density.

| Sample ID | OCT(Cl) | SPC | GDO | EtOH | PG | ETA | EDTA |
|---|---|---|---|---|---|---|---|
| Sample 61 | 2.27 | 42.37 | 42.37 | 6.50 | 6.50 | — | — |
| Sample 62 | 2.27 | 42.36 | 42.36 | 6.50 | 6.50 | 0.008 | 0.010 |

FIG. 3 presents the octreotide assay at different storage time points. As shown, the presence of 0.01 wt % (100 ppm) of EDTA solubilized in the lipid formulation with the help of ETA significantly enhanced the long-term peptide stability in pre-filled syringes at the long-term 25° C./60% RH storage condition.

Example 10. Stability of OCT(Cl) in Lipid Formulations in the Presence of Iron and EDTA Lipid formulations containing OCT(Cl) and different amounts of $Fe^{3+}$ and EDTA were prepared according to the compositions given in Table 10. Formulations were divided into sterilized 2R glass vials (0.5 g of formulation per vial), sealed and placed in a controlled environment storage cabinet at 40° C./75% RH. The head space of the vials was ambient air to ensure forced degradation conditions, i.e., no inert atmosphere such as nitrogen was introduced. At 1-month sampling point two vials of each formulation and storage condition were withdrawn from the controlled environment cabinet, equilibrated to room temperature for 1 hour and analyzed for peptide content (assay) using gradient HPLC with UV detection.

TABLE 10

OCT(Cl) containing FluidCrystal ® formulation compositions (in wt %) with different concentrations of $Fe^{3+}$ and EDTA. The octreotide content corresponds to 20 mg/mL octreotide free base when corrected for peptide content, purity and formulation density. The SPC/GDO weight ratio is 50/50 in all formulations.

| Sample ID | OCT(Cl) | SPC + GDO | EtOH | PG | EDTA | ETA | $FeCl_3 \times 6H_2O$* |
|---|---|---|---|---|---|---|---|
| Sample 63 | 2.27 | 84.73000 | 6.50 | 6.50 | — | — | — |
| Sample 64 | 2.27 | 84.72903 | 6.50 | 6.50 | — | — | 0.00097 |
| Sample 65 | 2.27 | 84.72758 | 6.50 | 6.50 | — | — | 0.00242 |
| Sample 66 | 2.27 | 84.72516 | 6.50 | 6.50 | — | — | 0.00484 |
| Sample 67 | 2.27 | 84.72541 | 6.50 | 6.50 | 0.00250 | 0.00209 | — |
| Sample 68 | 2.27 | 84.72444 | 6.50 | 6.50 | 0.00250 | 0.00209 | 0.00097 |
| Sample 69 | 2.27 | 84.72299 | 6.50 | 6.50 | 0.00250 | 0.00209 | 0.00242 |
| Sample 70 | 2.27 | 84.72057 | 6.50 | 6.50 | 0.00250 | 0.00209 | 0.00484 |
| Sample 71 | 2.27 | 84.71164 | 6.50 | 6.50 | 0.01000 | 0.00836 | — |
| Sample 72 | 2.27 | 84.71067 | 6.50 | 6.50 | 0.01000 | 0.00836 | 0.00097 |
| Sample 73 | 2.27 | 84.70922 | 6.50 | 6.50 | 0.01000 | 0.00836 | 0.00242 |
| Sample 74 | 2.27 | 84.70680 | 6.50 | 6.50 | 0.01000 | 0.00836 | 0.00484 |
| Sample 75 | 2.27 | 84.68409 | 6.50 | 6.50 | 0.02500 | 0.02091 | — |

TABLE 10-continued

OCT(Cl) containing FluidCrystal ® formulation compositions (in wt %) with different concentrations of $Fe^{3+}$ and EDTA. The octreotide content corresponds to 20 mg/mL octreotide free base when corrected for peptide content, purity and formulation density. The SPC/GDO weight ratio is 50/50 in all formulations.

| Sample ID | OCT(Cl) | SPC + GDO | EtOH | PG | EDTA | ETA | $FeCl_3 \times 6H_2O$* |
|---|---|---|---|---|---|---|---|
| Sample 76 | 2.27 | 84.68312 | 6.50 | 6.50 | 0.02500 | 0.02091 | 0.00097 |
| Sample 77 | 2.27 | 84.68167 | 6.50 | 6.50 | 0.02500 | 0.02091 | 0.00242 |
| Sample 78 | 2.27 | 84.67925 | 6.50 | 6.50 | 0.02500 | 0.02091 | 0.00484 |

*0.00097, 0.00242, and 0.00484 wt % of $FeCl_3 \times 6H_2O$ corresponds to 2, 5, and 10 ppm of $Fe^{3+}$, respectively.

FIG. 4 presents the octreotide assay at 1-month time point as a function of $Fe^{3+}$ concentration in the presence of different amounts of EDTA. As evident, with increasing the $Fe^{3+}$ concentration, more EDTA is needed to protect OCT from degradation. The protection against OCT degradation in the presence of $Fe^{3+}$ is enhanced with increasing EDTA concentration up to 100 ppm, followed by some decline between 100 and 250 ppm. There is also a clear correlation between $Fe^{3+}$ concentration and amount of EDTA needed to suppress the catalytic activity of iron. As shown in FIG. 5, a maximum stabilization effect is achieved starting from EDTA:$Fe^{3+}$ molar ratio of about 2:1. This corresponds to about 100 ppm EDTA at a $Fe^{3+}$ content of 10 ppm.

Example 11. Stability of OCT(Cl) in Lipid Formulations with EDTA and Iron in the Absence and Presence of ETA Lipid formulations containing EDTA or EDTA(Na) in the absence and presence of ETA were prepared according to the compositions given in Table 11. As shown in Example 1, neither EDTA(Na) nor EDTA are soluble in EtOH/PG without using ETA. EDTA(Na) was also insoluble in EtOH/PG even in the presence of ETA as assessed by visual inspection. Therefore, EDTA(Na), EDTA and EDTA(Na)/ETA containing mixtures in EtOH/PG were additionally filtered using a Millex-LG hydrophilic PTFE 0.2 μm syringe filter to remove the non-dissolved EDTA particles. After preparation, formulations were divided into sterilized 2R glass vials (0.5 g of formulation per vial), sealed and placed in a controlled environment storage cabinet at 40° C./75% RH. The headspace of the vials was ambient air to ensure forced degradation conditions, i.e., no inert atmosphere such as nitrogen was introduced. At predefined sampling points (up to two months of storage) two vials of each formulation and storage condition were withdrawn from controlled environment cabinets, equilibrated to room temperature for 1 hour and analyzed for peptide content (assay) using gradient HPLC with UV detection.

TABLE 11

OCT(Cl) containing lipid formulation compositions (in wt %) with different concentrations of $Fe^{3+}$ and EDTA. The octreotide content corresponds to 20 mg/mL octreotide free base when corrected for peptide content, purity and formulation density. The SPC/GDO weight ratio was 50/50 in all formulations.

| Sample ID | OCT(Cl) | SPC + GDO | EtOH | PG | EDTA | EDTA(Na) | ETA | $FeCl_3 \times 6H_2O$** |
|---|---|---|---|---|---|---|---|---|
| Sample 79 | 2.27 | 84.73 | 6.50 | 6.50 | — | — | — | — |
| Sample 80* | 2.27 | 84.72 | 6.50 | 6.50 | — | 0.01 | — | 0.00242 |
| Sample 81* | 2.27 | 84.71 | 6.50 | 6.50 | — | 0.01 | 0.00840 | 0.00242 |
| Sample 82* | 2.27 | 84.72 | 6.50 | 6.50 | 0.01 | — | — | 0.00242 |
| Sample 83 | 2.27 | 84.71 | 6.50 | 6.50 | 0.01 | — | 0.00840 | 0.00242 |

*For preparation of these formulations, EDTA mixtures in EtOH/PG were filtered using Millex-LG hydrophilic PTFE 0.2 μm syringe filter to remove insoluble EDTA particles.
**0.00242 wt % of $FeCl_3 \times 6H_2O$ corresponds to 5 ppm of $Fe^{3+}$.

FIG. 6 presents the assay and Stability Index values of octreotide as a function of time, respectively. As seen, only EDTA solubilized in the lipid formulation with the help of ETA dramatically enhanced the peptide stability compared to the reference formulation in the presence of 5 ppm $Fe^{3+}$. Under the same conditions, formulations containing EDTA (Na), EDTA or EDTA(Na)/ETA showed negative effect on OCT(Cl) stability (vs. the reference formulation).

Example 12. Effect of Different Alkylamines and Solvents on Stability of OCT(Cl) in Lipid Formulations with EDTA Lipid formulations were prepared according to the compositions given in Table 12. Formulations were divided into sterilized 2R glass vials (0.5 g of formulation per vial), sealed and placed in a controlled environment storage cabinet at 40° C./75% RH. The headspace of the vials was ambient air to ensure forced degradation conditions, i.e., no inert atmosphere such as nitrogen was introduced. At predefined sampling points (up to two months of storage) two vials of each formulation and storage condition were withdrawn from the controlled environment cabinets, equilibrated to room temperature for 1 hour and analyzed for peptide content (assay) using gradient HPLC with UV detection.

TABLE 12

OCT(Cl) containing lipid formulation compositions (in wt %). The octreotide content corresponds to 20 mg/mL octreotide free base when corrected for peptide content, purity and formulation density. The SPC/GDO weight ratio was 50/50 and ETA:EDTA, DiETA:EDTA, and ethylenediamine:EDTA molar ratios were 4:1 in all formulations.

| Sample ID | OCT(Cl) | SPC + GDO | EtOH | PG | EDTA | ETA | DiETA | Ethylene diamine |
|---|---|---|---|---|---|---|---|---|
| Sample 84 | 2.27 | 84.71160 | 6.50 | 6.50 | 0.01 | 0.0084 | — | — |
| Sample 85 | 2.27 | 84.70560 | 6.50 | 6.50 | 0.01 | — | 0.01440 | — |
| Sample 86 | 2.27 | 84.71180 | 6.50 | 6.50 | 0.01 | — | — | 0.00820 |

FIG. 7 presents the octreotide assay at different storage time points. As shown, the different alkylamines (ETA, DiETA or ethylenediamine) used to solubilize 0.01 wt % (100 ppm) of EDTA into the lipid formulations enhanced the peptide stability to a similar high degree when compared to the reference formulation. The obtained results also show that the positive effect of EDTA on the stability of OCT(Cl) is independent on the mixture used to prepare the lipid formulations as indicated by the data for EtOH/PG containing formulations in FIG. 8 when compared with FIG. 11.

Example 13. Stability of SOM(Cl) in Lipid Formulations in the Presence of EDTA Lipid formulations containing SOM(Cl) in the absence and presence of 100 ppm EDTA using EtOH/PG were prepared according to the compositions given in Table 13. Formulations were divided into sterilized 2R glass vials (0.5 g of formulation per vial), sealed and placed in controlled environment storage cabinets at either 40° C./75% RH or 25° C./60% RH. The head space of the vials was ambient air to ensure forced degradation conditions, i.e., no inert atmosphere such as nitrogen was introduced. At predefined sampling points (up to three months of storage) two vials of each formulation and storage condition were withdrawn from the controlled environment cabinets, equilibrated to room temperature for 1 hour and analyzed for peptide content (assay) using gradient HPLC with UV detection.

TABLE 13

SOM(Cl) containing lipid formulation compositions (in wt %) without and with EDTA. The SPC/GDO weight ratio was 50/50 in all formulations.

| Sample ID | SOM(Cl) | SPC + GDO | EtOH | PG | EDTA | ETA |
|---|---|---|---|---|---|---|
| Sample 89 | 2.00 | 86.00000 | 10.00 | 2.00 | — | — |
| Sample 90 | 2.00 | 85.98164 | 10.00 | 2.00 | 0.01000 | 0.00836 |

FIG. 9 presents the SOM assay at different storage time points and storage conditions. As shown, independently of solvent mixture used to prepare the lipid formulations, the presence of 100 ppm of EDTA solubilized in the lipid formulation by the use of ETA dramatically enhanced the peptide stability at both 40° C./75% RH and 25° C./60% RH storage conditions.

Example 14. Lipid Oxidation in Placebo Lipid Formulations in the Presence of EDTA Lipid placebo formulations in the absence and presence of 100 ppm EDTA were prepared according to the compositions given in Table 14. Formulations were divided into sterilized 2R glass vials (1 g of formulation per vial), sealed and placed in controlled environment storage cabinets at either 60° C./ambient RH or 40° C./75% RH. The headspace of the vials was ambient air to ensure forced lipid oxidation conditions, i.e., no inert atmosphere such as nitrogen was introduced. Some formulations also contained 5 ppm $Fe^{3+}$ to enhance the oxidative stress conditions (Table 14). At predefined sampling points (up to 9 days of storage at 60° C./ambient RH and up to 30 days of storage at 40° C./75% RH) two vials of each formulation were withdrawn from the controlled environment cabinets, equilibrated to room temperature for 1 hour and analyzed for oxygen concentration in the vial headspace (oxygen consumption is here used as an indirect measure of lipid oxidation in the lipid formulations) using a needle-type oxygen microsensor.

TABLE 14

Lipid formulation compositions (in wt %) without and with EDTA. The SPC/GDO weight ratio was 50/50 and 35/65 in Samples 103-106 and Samples 107-110, respectively.

| Sample ID | SPC | GDO | EtOH | EDTA | ETA* | $FeCl_3 \times 6H_2O$** |
|---|---|---|---|---|---|---|
| Sample 103 | 45.00 | 45.00 | 10 | — | — | — |
| Sample 104 | 45.00 | 45.00 | 10 | — | — | 0.00242 |
| Sample 105 | 44.99 | 44.99 | 10 | 0.01 | 0.0116 | — |
| Sample 106 | 44.99 | 44.99 | 10 | 0.01 | 0.0116 | 0.00242 |
| Sample 107 | 31.50 | 58.50 | 10 | — | — | — |
| Sample 108 | 31.50 | 58.50 | 10 | — | — | 0.00242 |
| Sample 109 | 31.49 | 58.49 | 10 | 0.01 | 0.0116 | — |
| Sample 110 | 31.49 | 58.49 | 10 | 0.01 | 0.0116 | 0.00242 |

*ETA:EDTA molar ratio is 5.5:1
**0.00242 wt % of $FeCl_3 \times 6H_2O$ corresponds to 5 ppm of $Fe^{3+}$

Example 15. DTPA Solubility as a Function of ETA/DTPA Molar Ratio 0.08 wt % DTPA solutions in EtOH/PG (50/50 w/w) were prepared in the absence and presence of various amounts of ETA added at different ETA/DTPA molar ratios (Table 15). The results show that DTPA is not soluble in EtOH/PG without using ETA. The obtained results also show that about 4.3 mol of ETA per 1 mol of DTPA is close to the required minimum amount needed to solubilize DTPA in the non-aqueous solvent used.

TABLE 15

Solubility of 0.08 wt % DTPA in EtOH/PG as a function of ETA/DTPA molar ratio.

| Sample ID | ETA/DTPA (mol/mol) | DTPA solubility (ca 24 h mixing) |
|---|---|---|
| Sample 111 | 0.0 | Not soluble |
| Sample 112 | 1.7 | Not soluble |
| Sample 113 | 4.3 | Soluble |
| Sample 114 | 4.8 | Soluble |

TABLE 15-continued

Solubility of 0.08 wt % DTPA in EtOH/PG as a function of ETA/DTPA molar ratio.

| Sample ID | ETA/DTPA (mol/mol) | DTPA solubility (ca 24 h mixing) |
|---|---|---|
| Sample 115 | 6.2 | Soluble |
| Sample 116 | 7.9 | Soluble |

The invention claimed is:

1. A pre-formulation comprising:
   a) 20-90 wt % of a diacyl glycerol;
   b) 20-80 wt % of a phospholipid selected from the group consisting of a phosphatidyl choline (PC), a phosphatidyl ethanolamine (PE), and a phosphatidyl inositol (PI);
   c) 1-30 wt % of a biocompatible, organic solvent selected from the group consisting of ethanol, propanol, isopropanol, benzyl alcohol, a polar co-solvent, and mixtures thereof;
   d) 0.001 to 0.05 wt % ethylenediaminetetraacetic acid (EDTA); and
   e) 0.1-12 wt % of at least one somatostatin receptor agonist or salt thereof;
   wherein the pre-formulation has a water content in the range of 0 to 1.0 wt %,
   wherein the pre-formulation further comprises an alkylamine selected from the group consisting of ethanolamine (ETA), diethanolamine (DiETA), meglumine, tris-hydroxymethylamine (TRIS), ethylenediamine, and serinol,
   wherein the molar ratio of EDTA:alkylamine is 1:≥3.0 for ETA, DiETA, meglumine, TRIS, and serinol, and 1:≥2.0 for ethylenediamine.

2. A pre-filled administration device containing a pre-formulation of claim 1.

3. A kit comprising the pre-filled administration device of claim 2.

4. A method of reducing oxidation of at least one active agent in a pre-formulation comprising:
   a) 20-90 wt % of a diacyl glycerol;
   b) 20-80 wt % of a phospholipid selected from the group consisting of a phosphatidyl choline (PC), a phosphatidyl ethanolamine (PE), and a phosphatidyl inositol (PI);
   c) 1-30 wt % of a biocompatible, organic solvent selected from the group consisting of ethanol, propanol, isopropanol, benzyl alcohol, a polar co-solvent, and mixtures thereof;
   d) 0.001 to 0.05 wt % of ethylenediaminetetraacetic acid (EDTA); and
   e) 0.1-12 wt % of a somatostatin receptor agonist or salt thereof;
   wherein the pre-formulation has a water content in the range of 0 to 1.0 wt %,
   wherein the pre-formulation further comprises an alkylamine selected from the group consisting of ethanolamine (ETA), diethanolamine (DiETA), meglumine, tris-hydroxymethylamine (TRIS), ethylenediamine, and serinol,
   wherein the molar ratio of EDTA:alkylamine is 1:≥3.0 for ETA, DiETA, meglumine, TRIS, and serinol, and 1:≥2.0 for ethylenediamine.

5. A process for preparing a pre-formulation of claim 1 comprising the steps of
   dispersing EDTA or a hydrate thereof and the alkylamine in the biocompatible organic solvent to produce a dispersion;
   mixing the dispersion until the EDTA and the alkylamine are fully dissolved to produce a mixture; and
   adding the at least one diacyl glycerol, the at least one phospholipid, and the at least one somatostatin receptor agonist or salt thereof to the mixture to produce the pre-formulation.

6. The pre-formulation of claim 1, wherein component a) comprises glycerol dioleate (GDO).

7. The pre-formulation of claim 1, wherein component a) is present in an amount of 20-60 wt %.

8. The pre-formulation of claim 1, wherein component b) comprises a PC.

9. The pre-formulation of claim 1, wherein component b) is present in an amount of 20-60 wt %.

10. The pre-formulation of claim 1, wherein component c) comprises ethanol.

11. The pre-formulation of claim 1, wherein component c) comprises propylene glycol.

12. The pre-formulation of claim 11, wherein the propylene glycol is present in an amount of 2-12 wt %.

13. The pre-formulation of claim 1, wherein component c) comprises a mixture of ethanol and propylene glycol.

14. The pre-formulation of claim 1, wherein component c) is present in an amount of 2-20 wt %.

15. The pre-formulation of claim 1, wherein the EDTA is present in an amount of 0.001-0.02 wt %.

16. The pre-formulation of claim 1, wherein the EDTA is present in an amount of 0.001-0.015 wt %.

17. The pre-formulation of claim 1, wherein component e) is selected from the group consisting of SST-14, SST-28, lanreotide, vapreotide, pasireotide (SOM230), and mixtures thereof.

18. The pre-formulation of claim 1, wherein component e) comprises somatostatin-14 chloride.

19. The pre-formulation of claim 1, wherein component e) consists of somatostatin-14 chloride.

20. The pre-formulation of claim 1, wherein component e) is present in an amount of 0.5-9 wt %.

21. The pre-formulation of claim 1, wherein component e) is present in an amount of 5 to 100 mg/mL.

22. The pre-formulation of claim 1, wherein component e) is present in an amount of 10 to 80 mg/mL.

23. The pre-formulation of claim 1, wherein the alkylamine is ETA.

24. The preformulation of claim 1, wherein the alkylamine is DiETA.

25. The pre-formulation of claim 23, wherein the equivalents of ETA relative to the amount of EDTA is in the range of 3.5 to 7 (mol/mol).

26. The pre-formulation of claim 23, wherein the equivalents of ETA relative to the amount of EDTA is in the range of 3.5 to 5 (mol/mol).

27. The pre-formulation of claim 1, wherein the EDTA and the alkylamine form an alkyl ammonium EDTA salt.

28. The pre-formulation of claim 27, wherein the alkyl ammonium EDTA salt is present in an amount of 0.001 to 0.02 wt % of the pre-formulation, calculated in terms of EDTA free acid.

29. The pre-formulation of claim 27, wherein the alkyl ammonium EDTA salt is present in an amount of 0.008 to 0.012 wt % of the pre-formulation, calculated in terms of EDTA free acid.

30. A medicament comprising the pre-formulation of claim 1.

31. The medicament of claim 30, wherein component b) is phosphatidyl choline (PC), component e) is selected from the group consisting of SST-14, SST-28, lanreotide, vapreotide, pasireotide (SOM230), and mixtures thereof, and the pre-formulation further comprises ethanolamine (ETA).

32. The medicament of claim 31, wherein the molar ratio of EDTA:ETA is 1:≥3.0.

* * * * *